(12) United States Patent
Alber et al.

(10) Patent No.: US 12,087,454 B2
(45) Date of Patent: Sep. 10, 2024

(54) SYSTEMS AND METHODS FOR THE DETECTION AND CLASSIFICATION OF BIOLOGICAL STRUCTURES

(71) Applicant: Aignostics GmbH, Berlin (DE)

(72) Inventors: Maximilian Alber, Berlin (DE); Roman Schulte-Sasse, Berlin (DE); Viktor Matyas, Frankfurt am Main (DE); Sharon Ruane, Berlin (DE); Cornelius Böhm, Berlin (DE)

(73) Assignee: Aignostics GmbH, Berlin (DE)

( * ) Notice: Subject to any disclaimer, the term of this patent is extended or adjusted under 35 U.S.C. 154(b) by 0 days.

(21) Appl. No.: 18/513,122

(22) Filed: Nov. 17, 2023

(65) Prior Publication Data
US 2024/0170165 A1 May 23, 2024

Related U.S. Application Data

(60) Provisional application No. 63/426,272, filed on Nov. 17, 2022.

(51) Int. Cl.
G16B 15/00 (2019.01)
G06T 7/00 (2017.01)
G16H 70/60 (2018.01)

(52) U.S. Cl.
CPC .......... G16H 70/60 (2018.01); G06T 7/0012 (2013.01); G16B 15/00 (2019.02); G06T 2207/20084 (2013.01); G06T 2207/30024 (2013.01)

(58) Field of Classification Search
CPC ...... G16H 70/60; G16B 15/00; B06T 7/0012; B06T 2207/30024; G06T 2207/20084
See application file for complete search history.

(56) References Cited

U.S. PATENT DOCUMENTS

| | | |
|---|---|---|
| 9,697,582 B2 | 7/2017 | Grunkin et al. |
| 10,544,467 B2 * | 1/2020 | Zhang .............. G01N 33/57438 |
| 10,572,996 B2 | 2/2020 | Eurèn |
| 10,580,128 B2 | 3/2020 | Miller |
| 10,803,586 B1 | 10/2020 | Reunanen et al. |
| 10,964,001 B2 | 3/2021 | Miller |
| 11,017,532 B1 | 5/2021 | Beck et al. |
| 11,080,855 B1 | 8/2021 | Beck et al. |
| 11,195,279 B1 | 12/2021 | Beck et al. |

(Continued)

OTHER PUBLICATIONS

Bejnordi, B. E. et al., "Diagnostic Assessment of Deep Learning Algorithms for Detection of Lymph Node Metastases in Women with Breast Cancer", JAMA | Original Investigation, vol. 318, No. 22, (2017), pp. 2199-2210.

(Continued)

Primary Examiner — Tsung Yin Tsai
(74) Attorney, Agent, or Firm — Finnegan, Henderson, Farabow, Garrett & Dunner LLP

(57) ABSTRACT

A classification model for identifying or classifying biological structures depicted in a base image can be generated by training a label generation model and then using the label generation model to train the classification model. The label generation model can be configured to accept co-registered base and informer images, while the classification model can be configured to accept base images. The classification model can output an indication when a biological structure is identified or classified in a base image.

30 Claims, 11 Drawing Sheets

(56) References Cited

U.S. PATENT DOCUMENTS

| | | | |
|---|---|---|---|
| 11,222,415 B2* | 1/2022 | Ozcan | G06T 5/60 |
| 11,276,165 B2 | 3/2022 | Thagaard et al. | |
| 11,307,142 B2 | 4/2022 | Miller et al. | |
| 2010/0111396 A1* | 5/2010 | Boucheron | G06F 18/29 |
| | | | 382/133 |
| 2018/0010192 A1* | 1/2018 | Zhang | C12Q 1/6886 |
| 2018/0094325 A1* | 4/2018 | Zhang | G16B 40/00 |
| 2019/0333199 A1* | 10/2019 | Ozcan | G06T 5/70 |
| 2019/0371425 A1 | 12/2019 | Kuo et al. | |
| 2019/0384047 A1* | 12/2019 | Johnson | G01N 15/1429 |
| 2020/0256867 A1 | 8/2020 | Hennek et al. | |
| 2021/0223254 A1 | 7/2021 | Wood et al. | |
| 2021/0312620 A1 | 10/2021 | Zuo et al. | |
| 2022/0044397 A1 | 2/2022 | Ceballos Lentini et al. | |
| 2022/0058839 A1* | 2/2022 | Chang | G06N 3/047 |
| 2022/0108123 A1 | 4/2022 | Bhargava et al. | |
| 2023/0007982 A1* | 1/2023 | Cherubini | G06T 7/73 |

OTHER PUBLICATIONS

Diao, J. A. et al., "Human-interpretable image features derived from densely mapped cancer pathology slides predict diverse molecular phenotypes", Nature Communications, vol. 12, (2021), 15 pages.
Mrowiec, T. et al., Immunohistochemistry-informed AI systems for improved characterization of tumor-microenvironment in clinical non-small cell lung cancer H&E samples, Poster Presentations—Proffered Abstracts, AACR Abstract S8 (submitted), (Jun. 15, 2022), Cancer Research, vol. 82, (Issue 12 Supplement), pp. 457.

\* cited by examiner

SYSTEMS AND METHODS FOR THE DETECTION AND CLASSIFICATION OF BIOLOGICAL STRUCTURES

CROSS-REFERENCE TO RELATED APPLICATIONS

This application claims the benefit of U.S. Provisional Application No. 63/426,272, filed Nov. 17, 2022. The provisional application identified above is incorporated here by reference in its entirety.

TECHNICAL FIELD

The present disclosure relates to systems and methods for the detection and classification of biological structures. In particular, the detection and classification of biological structures using machine learning models.

BACKGROUND

Pathology is a broad science involving the study of surgically removed human tissues and fluids to understand their structure, morphology and chemistry in both healthy and unhealthy conditions. By understanding the constituents of regular healthy human physiology, irregularities relating to disease or injury can be identified and used to understand their causes, symptoms and progression. As a result, modern pathology plays a significant role in many medical diagnosis procedures.

SUMMARY

According to a first aspect of the disclosure, there is provided a method for generating a machine learning model for identifying or classifying biological structures depicted in a base image, comprising: obtaining a first training dataset, the first training dataset including first sets of coregistered images of biological structures, each first set including a first base image and a first informer image, and being associated with first label data; training, using the first training dataset, a label generation model, the label generation model configured to accept as input a second set of coregistered images and to produce as output second label data corresponding to the second set of coregistered images, the second set of coregistered images including a second base image and a second informer image; generating a second training dataset using the label generation model, the second training dataset including the second base images and the second label data; and training, using the second training dataset, a classification model configured to accept as input a third base image and to provide as output an indication when a biological structure is identified or classified in the third base image.

Optionally, the first training dataset is obtained by obtaining a preliminary dataset including fourth sets of images of the biological structures, each fourth set including a fourth base image and a fourth informer image; applying, for each fourth set, the fourth base image to an object detection model trained to detect the biological structures to generate the corresponding first base image, the first base image being a cropped version of the fourth base image; and generating the first sets of the coregistered images of the biological structures using the fourth informer images and the first base images.

Optionally, the first training dataset is further obtained by filtering the first base images based on: misalignment with corresponding cropped versions of the fourth informer images; depiction of necrotic tissue or anthracosis deposits; or a distance between a depicted biological structure in a first base image and a biological tissue border; or the second training dataset is further generated by filtering the second base images based on: depiction of necrotic tissue or anthracosis deposits; or a distance between a depicted biological structure in a second base image and a biological tissue border.

Optionally, the first training dataset is further obtained by filtering the first base images using exclusion rules; or the second training dataset is further generated by filtering the second base images using the exclusion rules.

Optionally, the first training dataset is obtained by: applying detection rules to a preliminary dataset including fourth sets of images of the biological structures, each fourth set including a fourth base image and a fourth informer image, to generate the corresponding first base image, the first base image being a cropped version of the fourth base image.

Optionally, the first training dataset is obtained by: generating the first label data by applying labeling rules to the first sets of coregistered images of the biological structures.

Optionally, the labeling rules depend upon at least one of cell nucleus size, hematoxylin stain intensity of cell nucleus in H&E stain, sphericity or circularity of the nucleus, estimation of the cytoplasm region and cytoplasm stain intensity, eosin staining intensity of cytoplasm in H&E stain, ratio of estimated cytoplasm size to the cell nucleus size.

Optionally, the second base image comprises an image of biological material stained with hematoxylin and eosin; the second informer image comprises an image of the biological material stained with at least one of an immunohistochemistry stain, an immunofluorescence stain, or a multi-chromogenic immunofluorescence stain; and the biological material is stained with the at least one of the immunohistochemistry stain, the immunofluorescence stain, or the multi-chromogenic immunofluorescence stain after application of a removal agent to the biological material to remove the hematoxylin and eosin stain.

Optionally, the second base image comprises an image of biological material stained with hematoxylin and eosin; the second informer image comprises an image of the biological material stained with an immunofluorescence stain; and the second base image is captured after the second informer image is captured.

Optionally, the label generation model or the classification model comprises a convolutional neural network, residual neural network, or transformer neural network.

Optionally, the biological structures comprise nuclei, tubuli, nerves, arteries or any other blood vessels, single cells, cells or glomeruli.

Optionally, the first label data, the second label data, or the indication comprises at least one of: a graphical effect overlaid on the first base image, the second base image, or the third base image, respectively; a graphical indicator or alphanumeric label associated with the first base image, the second base image, or the third base image, respectively; or one or more coordinates indicating locations of biological structures in the first base image, the second base image, or the third base image, respectively.

According to a second aspect of the disclosure, there is provided a system comprising: at least one processor; and at least one computer-readable medium containing instructions that, when executed by the at least one processor, cause the system to perform operations comprising: obtaining a first image stained using a first stain; generating an indication of a biological structure identified or classified in the first image by applying the first image to a classification model, the classification model trained to accept as input a second image stained using the first stain and produce as output an indication when a biological structure is identified or classified in the input second image, the classification model trained using a label generation model configured to accept as input a set of third images and produce as output label data, the set of third images including a third image stained with the first stain and a third image stained with a second stain; and providing the indication.

Optionally, the first image is obtained by: obtaining a fourth image; applying the fourth image to an object detection model trained to detect the biological structures to generate corresponding one or more candidate first images, the one or more candidate first images being cropped versions of the fourth image.

Optionally, the first image is obtained by filtering the one or more candidate first images based on: depiction of necrotic tissue or anthracosis deposits; or a distance between a depicted biological structure in a candidate first image and a biological tissue border.

Optionally, the first image is obtained by filtering the one or more candidate first images using exclusion rules.

Optionally, the third image stained with the first stain comprises an image of biological material stained with hematoxylin and eosin; the third image stained with the second stain comprises an image of the biological material stained with at least one of an immunohistochemistry stain, an immunofluorescence stain, or a multi-chromogenic immunofluorescence stain; and the biological material is stained with the at least one of the immunohistochemistry stain, the immunofluorescence stain, or the multi-chromogenic immunofluorescence stain after application of a removal agent to the biological material to remove the hematoxylin and eosin stain.

Optionally, the third image stained with the first stain comprises an image of biological material stained with hematoxylin and eosin; the third image stained with the second stain comprises an image of the biological material stained with an immunofluorescence stain; and the third image stained with the first stain is captured after the third image stained with the second stain is captured.

Optionally, the label generation model or the classification model comprises a convolutional neural network, residual neural network, or transformer neural network.

Optionally, the biological structures comprise nuclei, tubuli, nerves, arteries or any other blood vessels, single cells, cells or glomeruli.

Optionally, the indication comprises at least one of: a graphical effect overlaid on the first image; a graphical indicator or alphanumeric label associated with the first image; or one or more coordinates indicating locations of biological structures in the first image.

Optionally, the indication is provided to a display or user interface, a storage location, or a second system.

According to a third aspect of the disclosure, there is provided a computer-readable medium containing instructions that, when executed by at least one processor of a system, cause the system to perform operations comprising: obtaining a first image stained using a first stain; generating an indication of a biological structure identified or classified in the first image by applying the first image to a classification model, the classification model trained to accept as input a second image stained using the first stain and produce as output an indication when a biological structure is identified or classified in the input second image, the classification model trained using a label generation model configured to accept as input a set of third images and produce as output label data, the set of third images including a third image stained with the first stain and a third image stained with a second stain; and providing the indication.

Optionally, the first image is obtained by: obtaining a fourth image; applying the fourth image to an object detection model trained to detect the biological structures to generate corresponding one or more candidate first images, the one or more candidate first images being cropped versions of the fourth image.

Optionally, the first image is obtained by filtering the one or more candidate first images based on: depiction of necrotic tissue or anthracosis deposits; or a distance between a depicted biological structure in a candidate first image and a biological tissue border.

Optionally, the first image is obtained by filtering the one or more candidate first images using exclusion rules.

Optionally, the third image stained with the first stain comprises an image of biological material stained with hematoxylin and eosin; the third image stained with the second stain comprises an image of the biological material stained with at least one of an immunohistochemistry stain, an immunofluorescence stain, or a multi-chromogenic immunofluorescence stain; and the biological material is stained with the at least one of the immunohistochemistry stain, the immunofluorescence stain, or the multi-chromogenic immunofluorescence stain after application of a removal agent to the biological material to remove the hematoxylin and eosin stain.

Optionally, the third image stained with the first stain comprises an image of biological material stained with hematoxylin and eosin; the third image stained with the second stain comprises an image of the biological material stained with an immunofluorescence stain; and the third image stained with the first stain is captured after the third image stained with the second stain is captured.

Optionally, the label generation model or the classification model comprises a convolutional neural network, residual neural network, or transformer neural network.

Optionally, the biological structures comprise nuclei, tubuli, nerves, arteries or any other blood vessels, single cells, cells or glomeruli.

Optionally, the indication comprises at least one of: a graphical effect overlaid on the first image; a graphical indicator or alphanumeric label associated with the first image; or one or more coordinates indicating locations of biological structures in the first image.

Optionally, the indication is provided to a display or user interface, a storage location, or a second system.

Features from one or more aspects or any optional feature thereof may be combined together.

BRIEF DESCRIPTION OF THE DRAWINGS

The accompanying drawings, which comprise a part of this specification, illustrate several embodiments and, together with the description, serve to explain the principles and features of the disclosed embodiments. In the drawings.

DETAILED DESCRIPTION

Figure 1:
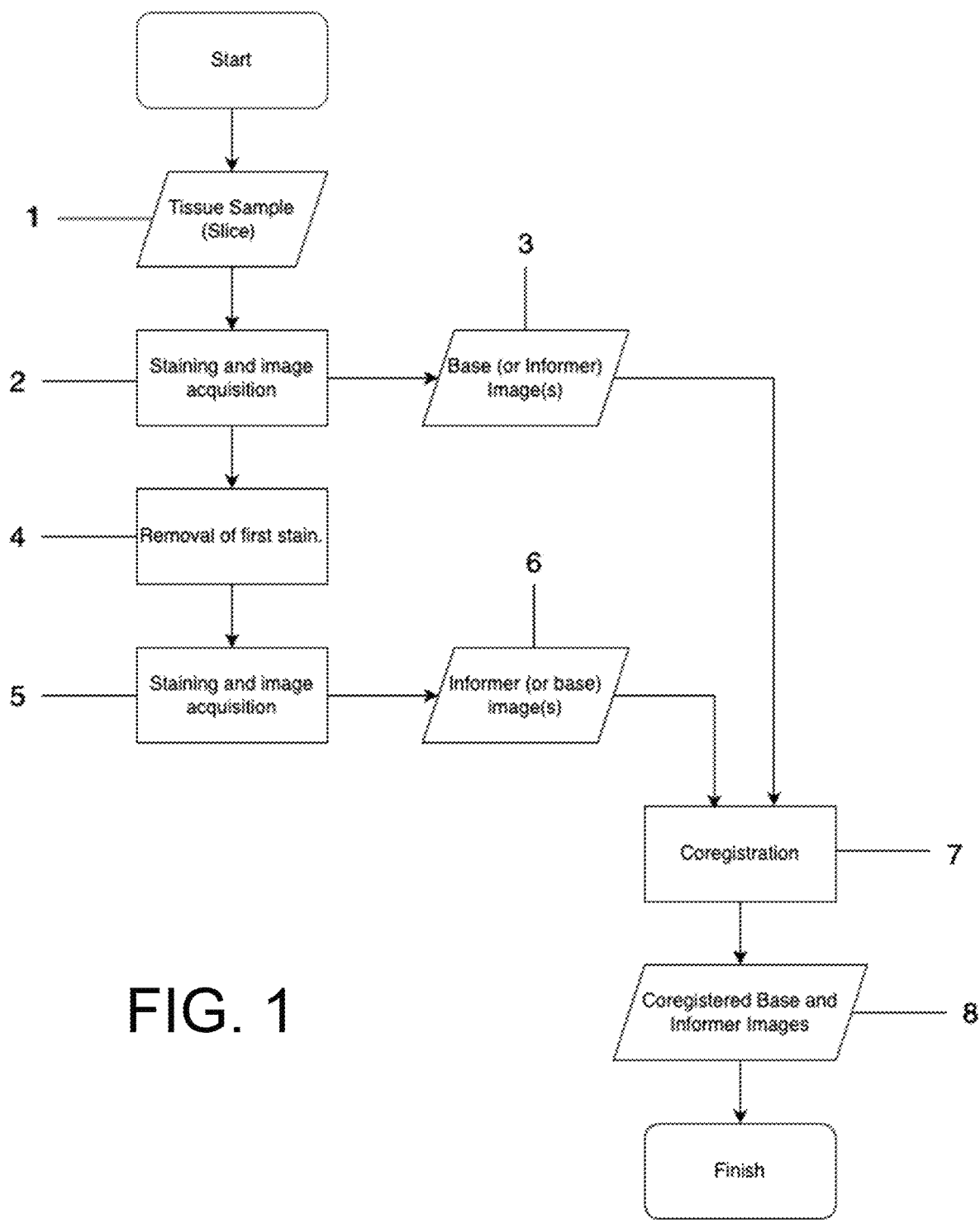
FIG. 1 shows a flow diagram of the tissue staining, image generation, and coregistration steps of the workflow, in accordance with disclosed embodiments.

Reference will now be made in detail to exemplary embodiments, discussed with regard to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

The study of human tissues and/or fluids at the microscopic scale is a frequently used tool in pathology. This type of examination allows for the identification and classification of different biological structures within the sample undergoing evaluation. To be examined under a microscope, the sample must be prepared to be sufficiently thin for light to penetrate. As most human tissue at this scale is essentially transparent, different types of tissue staining have been developed to highlight specific structures within the sample, enabling their identification. Modern pathology equipment is designed to capture detailed digital images of entire microscope slides (whole slide imaging) of human tissue.

Many types of staining have been developed which are specialized for different target structures. The most widely used staining technique at present combines two histological staining agents hematoxylin and eosin (H&E stain). The hematoxylin stains the cell nuclei purple/blue while the eosin stains the extracellular matrix and cytoplasm pink.

While these microscopic evaluation techniques play a key role in pathology, the explosion of innovations in biotechnology in recent decades has seen similar techniques being adopted for a wide range of applications including in-vitro and in-vivo research and development (R&D) for many varied purposes. Some examples (but not an exhaustive list) include drug development and research for new oncological therapies.

The task of interpreting and analyzing microscope images of human tissues or fluids typically requires a highly trained and experienced professional. In the case of pathology, this task will be performed by a qualified pathologist (R&D operations may implement alternative trained experts).

The process of a human expert assessing microscope images of whole-slides of human tissue is labor intensive, expensive and fraught with risk. The area which is analyzed is limited by the rate at which a human expert can process the highly detailed information contained within the image, thus limiting the proportion of the slide which can be included in the analysis. This limitation is further concentrated by a chronic lack of trained pathologists in almost all healthcare systems worldwide, combined with ever increasing workloads for these valuable experts. The evaluation of individual human experts is also highly subjective, with significant variations having been previously reported between the analysis results reported by different qualified pathologists when evaluating the same tissue samples. These sources of risk are less than ideal in a sector where the accuracy of results can have major implications for patients.

The inclusion of software analysis tools, in particular those incorporating machine learning techniques, into the analysis procedure for images of tissue slides offers great opportunities for improvement. These include alleviating the work-load for trained pathologists, increasing the quantity of information from each slide image used in the analysis process, and reducing the risk of human error in diagnosis.

Deep learning models for the detection and classification of biological structures in digital pathology have typically been trained using manually generated annotations based on a single H&E stain of each slide. This situation is not ideal because:

It is expensive.
Time consuming.
Pathologists are a very limited resource.
Rate of progress is limited by the above points.
Pathologists have differing opinions/human error or oversight.
Lack of clarity/accuracy in labeling creates label noise. This impacts on the
models which are trained on the data.

H&E staining is easily accessible, but often ambiguous. Other more complex/difficult/expensive stainings (sometimes combined with H&E) can reveal more information/remove the ambiguity. These other stainings may not however be suitable or realistic for routine use. In some limited examples, studies of human expert generated annotation have demonstrated that ambiguities and errors inherent in annotations made based purely on H&E staining of tissue can be greatly reduced if a secondary staining method is used to provide additional information to inform the annotating process. These studies have typically involved consecutive tissue slides taken from the same piece of material being given different stainings. The human expert annotator then studies the equivalent regions of the differently stained consecutive regions. By combining the information offered by the two different types of staining, ambiguity and errors are reduced and the quality of the annotations which are generated is improved. While this technique represents an improvement, there are still a number of significant limitations. One example is that by using consecutive tissue slides there are slight differences between the material which is stained in each image (certain objects may be present in one image, but not in the other. Objects may appear differently) this can impact on the quality of annotations. Another example of a limitation is that a high level of variation was noted between the results produced by different qualified pathologists examining the same tissue slides.

Digital microscope images of biological material can include biological material prepared for examination under the microscope. Such material can include, but is not limited to: whole slide images of tissue slides for microscopic pathology examinations, samples prepared for microscope examination for biotechnology research. Such material can include human tissue or non-human, animal tissue.

Biological structures can include identifiable features of interest within digital microscope images of biological samples. Such features can be indicative of normal or healthy biological processes or abnormal or pathological processes. Such features can include nuclei, tubuli, nerves, arteries or any other blood vessels, single cells, cells or glomeruli. This list is not exhaustive and other possibilities are also compatible with the disclosed technology.

A human annotator can be a pathologist, clinician, researcher or other suitably trained expert capable of identifying biological structures within digital microscope images of biological material.

A base image can be a digital microscope image of biological material. The biological material can be stained with one or more suitable histological stains (e.g., H&E, but others are possible, and included in the scope of this document). As may be appreciated, as an image obtained by using a limited palette of common and accessible stains, the base image may lack some information concerning biological structure(s) present in the biological material.

Informer image(s) can be one or more additional digital microscope images of the same biological material as the base image. In some instances, the informer image(s) can contain complementary information on the biological material which is absent from the base image. In various instances, the informer image(s) can emphasize or highlight information present in the base image. An informer image can therefore be used to reduce ambiguity and enhance the quantity and quality of information which can be extracted from the biological material being studied. Examples of potential informer images include, but are not limited to, digital microscope images of the biological material made under additional histological stainings including immunohistochemistry (IHC) stainings (single or multiplex chromogenic immunohistochemistry), multiplex immunofluorescence (mIF) stainings. An informer image may consist of several sub-images. For example, a multiplex immunofluorescence (mIF) image can include several sub-images or layers.

1. High-Level Technology Overview

The disclosed embodiments include an operational system 40 (which may also be described as an operational tool 40) for digital pathology based on trained machine learning models and a process for producing the same. The completed system 40 functions to identify and classify biological structures within base images 33 (typically digital microscope images of hematoxylin and eosin (H&E) stained biological material) with extremely high accuracy and a high processing rate. Consistent with disclosed embodiments, the system 40 can be adapted to perform a multitude of common tasks within the pathology sector. The system 40 can exhibit improved performance as compared with human pathologists, or as compared to conventional automated methods. The completed system 40 accepts base images 33 as input (typically tissue slides stained with the common H&E histological staining designed to reveal the structure). The system 40 can be trained to identify, or identify and classify, biological structures in the base image 33.

While the input to the finished system 40 is a base image 33, the data set used to train the classification model 30 for the system 40 is formed from a labeled set of object images 25. The labeled set of object images 25 are generated by extracting information from both base 3 and informer 6 images of the biological material 1 (multiple spatially resolved analysis techniques applied to the same tissue (commonly H&E and one or more other types of histologically stained images of the same tissue)). Using information from both base 3 and informer 6 images enhances the accuracy of the labeling process, generating higher quality labels than would be produced using only the base image 3.

The disclosed embodiments include embodiments in which the informer image 6 is a digital microscope image of the same biological material 1 as the base image 3. The base image 3 depicts the biological material 1 under a common and accessible histological staining (for example H&E). The informer image 6 depicts the same biological material 1 under a different histological staining (for example IHC or mIF) which offers additional information capable of resolving ambiguity within the base image 3. The order of creating the base 3 and informer 4 stainings can differ for different staining combinations and their specific characteristics. A stain removal step 4 can be carried out between the base 2 and informer 5 stainings and image generations to enable a good quality of the second staining and image generation process.

The inclusion of additional information extracted using the informer image(s) 6 in the label extraction process can create a training data set 25, that is improved over a training data set generated using only base image staining alone. The training data set 25 can associate the label data with the original base (typically H&E stained) image. The training data set 25 can be used to generate a classifier 30 configured to accept base images only, where the classifier 30 is improved and more accurate when compared to classifiers trained using base images 3 alone. The classifier 30 can therefore be trained using the additional information available extracted using the informer images 6, while remaining suitable for pathology workflows that use bases (typically H&E stained) images only.

The disclosed embodiments improve upon conventional approaches to building and training machine-learning actuated software tools for the enhanced analysis of digital microscope images of biological material. The disclosed embodiments include:
  a) systems and methods for the identification and classification of biological structures within base images 33 of biological material where the analysis process is based on a machine learning model 30 trained using labels obtained from one or more informer images 6.
  b) systems and methods for the automated extraction of labels for biological structures of interest identified within base images from at least one coregistered informer image 17.

As may be appreciated, the systems 40 and methods in a) can be used in combination with the systems and methods in b). In some embodiments, a) and b) can be implemented using different types of informer images 6 to improve upon the information available from the base image 3 alone. Various embodiments can use differing combinations of base image 3 and informer image 6 types. For example, as described in Section 2, the systems and methods of a) and b) can be implemented using immunohistochemistry (IHC) stained digital microscope images as the informer image(s) 6 and H&E staining for the base image 3. As an additional example, as described in Section 3, the systems and methods of a) and b) can be implemented using multiplex immunofluorescence (mIF) stained digital microscope images as the informer image(s) 6 and H&E staining as the base image 3. These examples are not intended to be exhaustive or limiting. The systems and methods of a) and b) can be applied for other combinations of stainings for the base 3 and informer 6 images.

The systems and methods of a) and b) can enable the labeling of targeted biological structures with improved accuracy and efficiency. The disclosed embodiments can offer improved accuracy and efficiency in the analysis of digital microscope images of stained biological tissue as compared with conventional techniques. Labels extracted using informer images 6, consistent with disclosed embodiments, can be subsequently used to train machine learning models for detection and classification of the target biological structures using the highly accessible base stain (typically H&E). Thus the disclosed systems and methods offer significant improvements in the efficiency and accuracy of the analysis of digital microscope images of biological material as compared with previously established procedures.

1.1 Brief Summary of a)

Contains: A method for the development of machine learning tools for the identification, classification and analysis of specific target biological structures within digital microscope images of biological material (base images). A system 40 for carrying out identification, classification and analysis on specific target biological structures within digital microscope images of biological material.

1.1.1 Method

Two subsections follow. The first describes a generalized method, including three machine learning models 10, 20, 30 which are implemented at different stages of the method. The second subsection describes a particular exemplary implementation of this method.

1.1.1.1 Stepwise Workflow Description

Consistent with disclosed embodiments, multiple data sources comprising at least one base image 3 and at least one informer image 6 of the same sample of biological material 1 can be used to generate training labels. Because the training labels are generated using information contained within the multiple data sources, the training labels can be more precise or accurate, enabling the training of machine learning models that provide improved identification and classification of targeted biological structures within digital microscope images of biological material. As may be appreciated, the following sequence of steps is not intended to be limiting. Consistent with disclosed embodiments, steps in this sequence can be combined or omitted, or new steps can be added.

i) Acquisition of at least one base image 3 and at least one informer image 6 of the same biological tissue 1: Thin samples of biological material 1 (tissue, fluid etc.) can be prepared in slides. At least one base image 3 and at least one informer image 6 of the same biological material 1 offering additional information complementary to the base image 3 can be obtained. The base stain is commonly an H&E stain, although other staining types can also be used. The base image 3 can contain incomplete information for labeling purposes. The informer image 6 can provide additional or complementary information suitable for use with the information provided by the base image 3 for labeling purposes. As may be appreciated, the informer image 6 can provide information that is absent or difficult to discern from the base image 3 alone (this can be seen clearly in FIGS. 8 and 9), and which is of value for the application being developed. The informer image 6 may be any other type of histological stain which differs from the base image stain and can provide additional information to complement the base image 3, and aid in the labeling of it. A flow diagram illustrating the workflow for tissue sample staining and image generation is shown in FIG. 1. (The ordering of the base and informer stainings is optional depending upon the technical requirements of the specific stain combinations used for a particular embodiment of the technology.)

FIG. 1 shows a flow diagram of the tissue staining, image generation, and coregistration 7 steps of the workflow described above (Steps i) and v)). The optional quality control steps ii) and iii) have been omitted from this representation. Note that the detection of objects in the base image 3 (step iv)) can be carried out either between the creation of the base image 3 and coregistration steps 7, or at a later point after coregistration 7 is complete. This step was omitted from this representation of the workflow as it is not a mandatory requirement to achieve the tissue staining and image generation workflow. The same symbols are used throughout this document to denote the same things: Rounded rectangles=start/finish, rectangles=process, parallelograms=information/data source. Please note that the process "Detection of objects of interest in base image" 5 can also be carried out after the coregistration step 7 has been completed.

ii) Quality Control image processing (OPTIONAL): confirms the images (or other spatially structured data sources) are usable: verifies magnification, checks for and removes blurriness or artifacts. The specific tools included in this step can vary depending on the specific embodiment of the technology. Different staining combinations, target biological structures or final goals in functionality can require different quality control steps for optimal performance.

iii) Automated data cleaning pipeline (OPTIONAL): removes tissue regions likely to interfere with correct label extraction. The specific tools included in this step can vary depending on the specific embodiment of the technology. Different staining combinations, target biological structures or final goals in functionality can require different data cleaning steps for optimal performance.

iv) Detection 15 of specific target biological structures within the base stained images 13: This can be done using automated methods or human expert annotations. An automated approach can provide superior results compared with the manual method (reduced bias, higher quality, faster production of larger data sets). Automated object detection can be based on a machine-learning model 10 (this model is hereafter referred to as Model 1 10).

iv-a) OPTION to carry out a similar detection step for biological structures also within the Informer Image 6. In some cases this can be used as a quality control method to cross validate the results obtained for object detection in the base image 3. The suitability of this approach is however heavily dependent upon the precise stainings being applied for the informer images 6, and the type(s) of objects which are being detected in images (for example, not every subtype of object present will be visible under certain types of informer stains).

v) Accurate coregistration 16 of base image(s) 3 and informer image(s) 6 of the same biological tissue 1: overlaying and aligning the base image(s) 3 and informer image(s) 6 of the same tissue 1. In some embodiments, step v) can be carried out before step iv) (as shown in FIG. 1 by reference numerals 7 and 8).

vi) Extraction from the coregistered informer stained images 17 of labels for the objects identified in step iv: The additional informer stained image(s) 6 contain valuable information which can facilitate the accurate labeling of the biological structures described in v). These labels can be extracted and transferred between the coregistered images 17 via one of several techniques:

Automated methods for label extraction: There are multiple approaches by which automated label extraction can be achieved (e.g., rule-based label extraction (for example based on thresholding) or more complex methods based on machine learning approaches). These are described in more detail in method b) below. Automated label extraction methods may accept the informer image 6 and the coregistered 17 base image 3 as input, or such methods may operate using only the informer image 6 as input. In some instances, higher quality results may be generated by including both the informer 6 and base images 3 as input. Thus this disclosure focuses primarily on the use of both coregistered images 17 as input, however the use of the informer image 6 alone is both valid and included in this technology description.

Human expert label extraction: manual annotation by multiple human experts using the information from the coregistered 17 informer stained image 6 to label the identified objects.

Automated label extraction methods offer advantages in efficiency and accuracy over manually extracted labels, however both approaches are valid for use in the method a) disclosed here.

The technology presently disclosed employs a deep-learning based machine learning approach to achieve automated label extraction (Step vi)). This represents the most innovative and technologically advanced of these techniques, and also offers the highest quality results. The machine learning model 20 used to extract the label data from the coregistered 17 base 3 and informer images 6 is hereafter referred to as Model 2 20 in this disclosure.

If rule-based or manually extracted label extractions are used instead of a deep-learning approach, then Model 2 20 is removed from the workflow and replaced with the alternative method. The alternative methods for the label extraction have been included for completeness to illustrate the full spectrum of possibilities. However, the most effective method which produces the highest quality results is the deep-learning based label extraction approach. For this reason we primarily focus on this approach in this disclosure.

vii) Training of a machine learning model 30 to identify and classify target biological structures in previously unseen base images 33 only: Parts of-or entire base images 25 showing the biological structures of interest which were labeled using the information extracted from the coregistered informer image 17 using during steps v) and vi) can be used to train a machine learning model 30 for the automated detection and classification of the target biological structures within base images 33 only. The trained machine learning model 34 can be incorporated into a system 40 which acts as a stand-alone tool for the detection of the target biological structures within digital microscope images of biological tissue. The completed system 40 can analyze digital microscope images of biological tissue with far greater speed and accuracy than human workers are capable of. This final machine learning model 30 is hereafter referred to in this disclosure as Model 3 30.

1.1.1.2 Brief Description of Machine Learning Models 1-3

Figure 2:
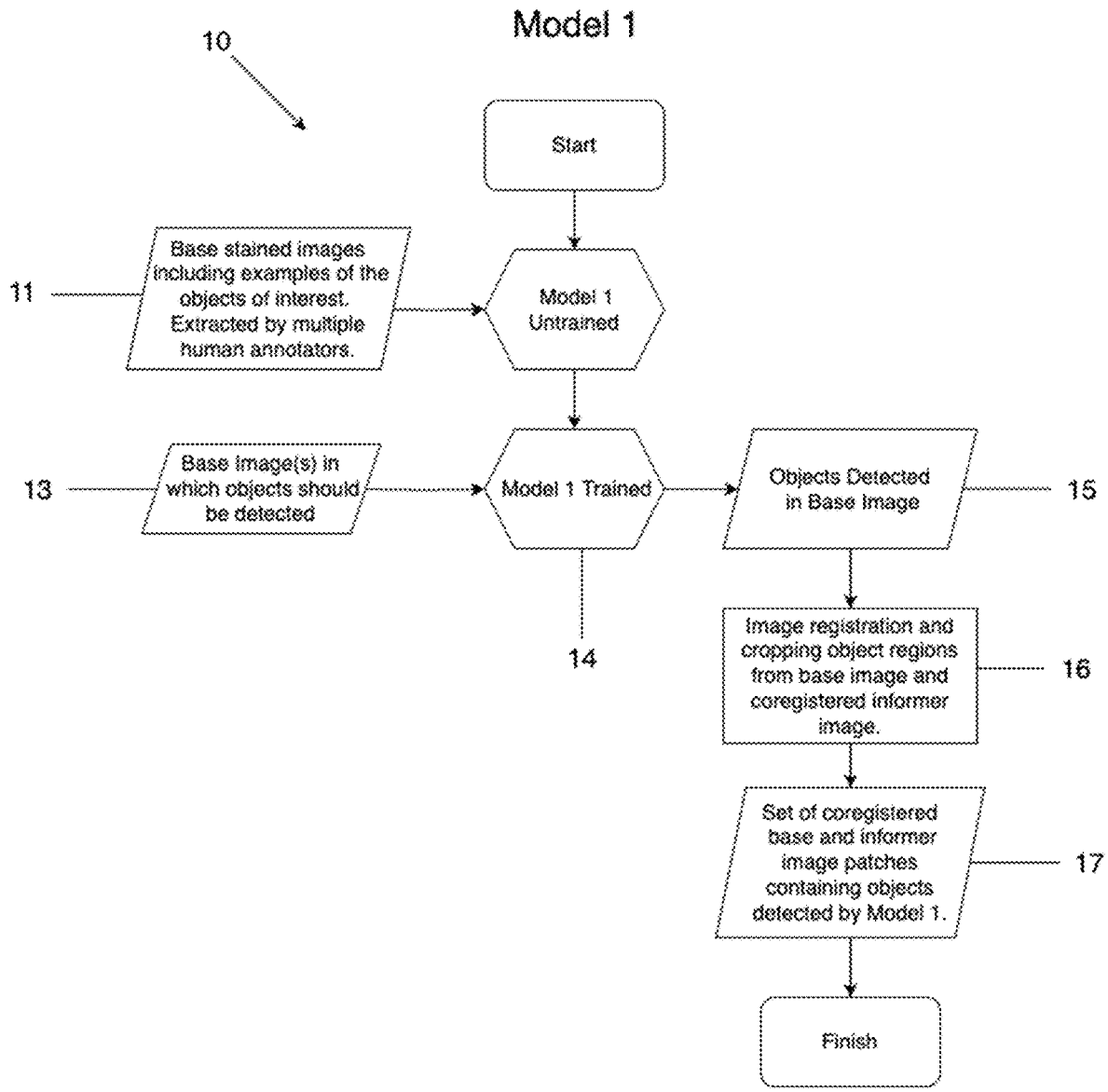
FIG. 2 shows a flow chart describing the workflow for Model 1, in accordance with disclosed embodiments.

Model 1 10 (Object Detection in Base Image):

This model 10 is trained using a set of base images 11 (e.g. H&E stained images) of the biological objects of interest (e.g. cells or other biological structures of interest). In some embodiments, the training image set 11 can be created using multiple human experts to negate the influence of individual biases. The trained Model 1 14accepts a base image 13 (e.g. H&E stained image of biological tissue) as input and locates the target objects of interest (for example cell nuclei) present with the image 15. The region surrounding each of these identified objects is then cropped 16 (from both the base (H&E) and coregistered informer (IHC) images) to produce a patch 17 containing the object. A large set of these objects are identified 15, cropped 16 and stored. It is this output of archived coregistered H&E and IHC image patches 17 of the objects of interest which form the input to Model 2 20. The workflow for training and implementation of Model 1 10 with associated processes for image coregistration and image patch cropping 16 is shown in FIG. 2. Note that image coregistration can alternatively be carried out before object detection is performed by Model 1 10 (as shown in FIG. 1 by reference numerals 7 and 8).

FIG. 2 shows a flow chart describing the workflow for Model 1 10. The same principles defined for the previous flow-diagram symbols apply, with the following additions: hexagon=machine learning model.

Model 2 20 (Label Generation Model):

As described at the start of section 1, the final operational system 40 for digital pathology which is produced by method a) contains a classification model 30 which is trained using labeled base images 25 (typically H&E stained) of the biological objects of interest. The labels for these training images 25 are obtained by consulting the information contained within both base (e.g., H&E stained) and informer images (e.g., IHC stained) of the same tissue to give exceptional accuracy as compared with labels extracted from base images alone.

As described in subsection 1.1.1.1 step vi), the label extraction process can be achieved via various methods. For example, one or more pathologists could manually examine the coregistered (spatially aligned) base and informer images of each object, or an automated rule-based label extraction technique could be used. Alternatively, a deep-learning approach to label extraction can be used. Model 2 20 is the model used to realize this deep-learning approach for label extraction from coregistered base and informer images 17 of the same biological structures of interest.

Figure 3:
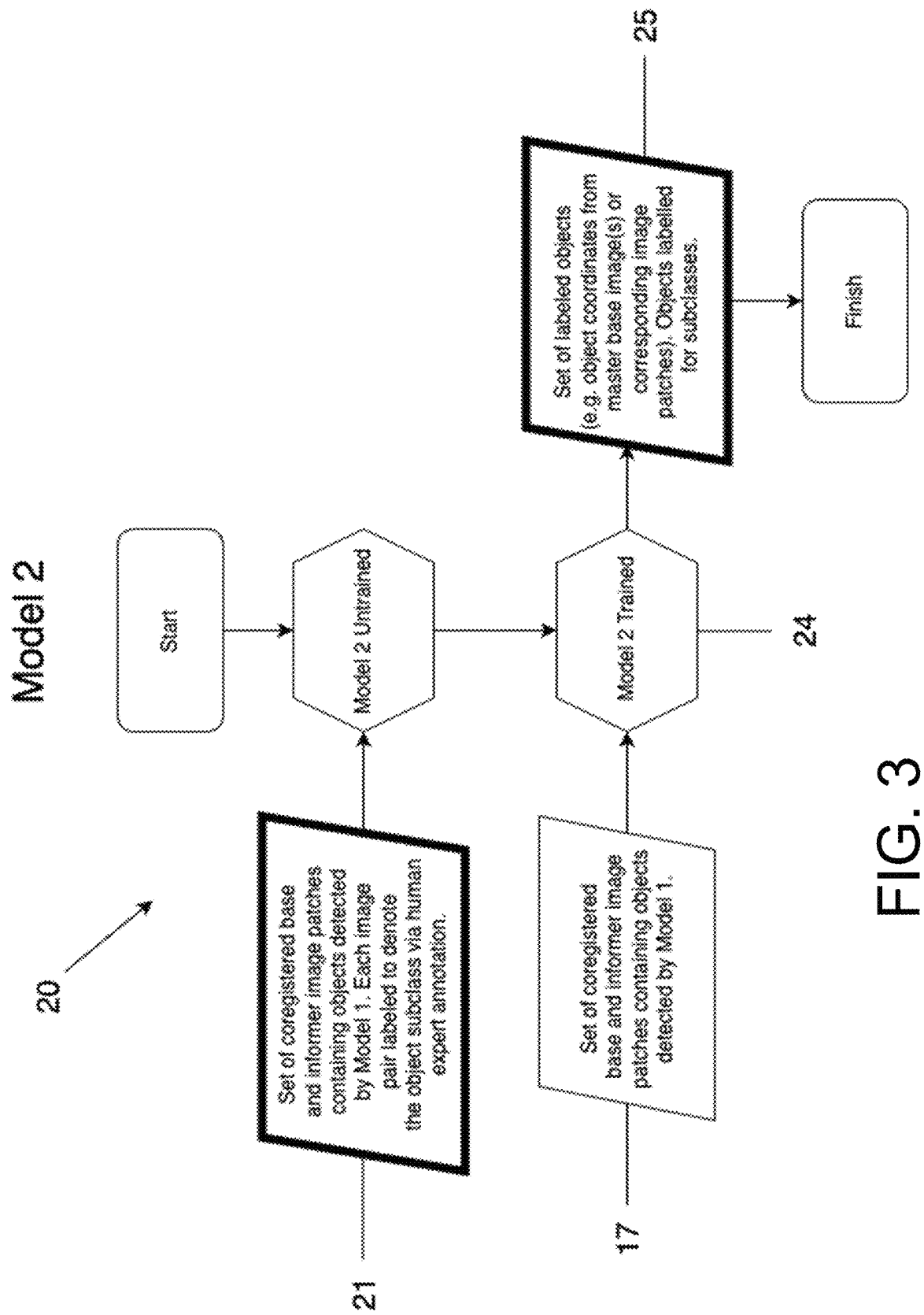
FIG. 3 shows a flow diagram describing the workflow for the training and implementation of Model 2, in accordance with disclosed embodiments.

Model 2 20 can be used to automate the extraction of labels from stacked base and informer image patches 17 of the same objects of interest identified by Model 1 10 (Model 2 20 can also be configured to operate on informer images only, instead of stacked informer and base images 17, with a slight reduction in performance), these labels are of high quality due to the use of the stacked base and informer image patches 17. Consistent with disclosed embodiments, Model 2 20 can allocate labels to images with greater accuracy than would otherwise be possible via purely manually allocated labels or rule-based label generation. Model 2 20 can provide superior output compared to other techniques and can generate large quantities of accurately labeled data quickly. The workflow for training and implementation of Model 2 20 is shown in FIG. 3 by a flow diagram. The same principles defined for the previous flow-diagram symbols apply, with the following addition: a thick border on a parallelogram denotes that the data has been labeled to denote subclasses.

Consistent with disclosed embodiments, the training data 21 for Model 2 20 can be generated by human experts. The human experts can manually annotate base images of the objects of interest (allocating labels to denote different subclasses of the objects) by examining the clues offered by both the base (H&E stained) image of each object and also the coregistered informer (IHC stained) images of the same object. By consulting both the IHC and H&E stained image of the object when annotating, the human experts can reduce ambiguity and errors which would occur if they only consulted the base (H&E) image. By using annotations generated by multiple pathologists, biasing effects of individual judgment and skill are compensated for in the final output training data set 21. The outcome of this stage can be a training data set 21 representing a large number of individual objects of interest. For each object of interest in the set there is an H&E stained image of the region containing the object, an IHC stained image of the same region containing the object, and a label classifying which subset the object belongs to. Model 2 20 can then be trained using stacked H&E and IHC images for each object along with the human-annotator-generated label for the object.

Once trained, Model 2 20 can provide highly accurate label extraction with high through-put. The trained model 24 accepts as input stacked H&E and IHC stained image patches 17 of the same tissue region containing an object of interest (e.g. a cell). The output 25 of the model 20 is a classification label for the object of interest contained within the stacked images. The final result of running this model 20 on an image patch dataset 17 is a set of labeled base images 25 of objects of interest. Thus, the trained model 24 replaces and improves upon both human pathologist annotation and rule-based label extraction techniques. Additional value arises from the use of Model 2 20 to generate the labeled training data 25 for Model 3 30 using the information contained within both H&E and IHC staining of the same tissue, as the labeled training data 25 is of high quality.

Model 3 30 (Operational Base Image Classifier Model):

Consistent with disclosed embodiments, Model 3 30 can accept base (typically H&E stained) images 33 and identify, or identify and classify, biological structures in these base images. As may be appreciated, Model 3 30 can be central to a digital pathology system 40 (e.g., as described in section 1.1.2). The creation of Model 3 30 can be the result of the activities described in section 1.1.1. Model 3 30 can be trained upon the high quality labeled base image sets 25 produced by Model 2 20 using the information contained within both base and informer images. However, in contrast to Model 2 20, Model 3 30 may not accept as input informer (IHC stained) images and may not include such images in the training or operational stages. Base (H&E stained) images of the objects and the labels ascribed to them by Model 2 20 are used together as the training data 25 for Model 3 30. The labels themselves are of extremely high quality due to the inclusion of the informer image (IHC stain) information in the label generation process, but the informer (IHC stained) images themselves may not be directly used in the training or implementation of Model 3 30.

Once trained, Model 3 30 can accept base (H&E stained) images of objects as input 33. Model 3 30 can be trained to identify, or identify and classify, certain biological structures in these images. The trained model 34 can be suitable for the detection and classification of the object of interest in base (typically H&E stained) images 33 alone. It can accurately classify these objects into appropriate subsets due to the high quality training data 25 produced by Model 2 20 using the information from both the informer image as well as the base image to inform the labeling process. The completed 34 Model 3 30 can combine the ability to operate purely on base (H&E) input images 33 with the high accuracy offered by the use of training data 25 generated by a machine learning based approach informed by both base 3 and informer 6 image information.

Model 3 30 can operate on H&E images and produce high quality results. H&E stained images are extremely common in pathology, making Model 3 30 usable in many situations and locations, without being limited to laboratories with access to more advanced techniques. Model 3 30 can therefore be integrated into existing pathology workflows that rely on H&E images, providing improved accuracy to these workflows, without the difficulty or complexity of integrating other stainings such as IHC or mIF images.

Figure 4:
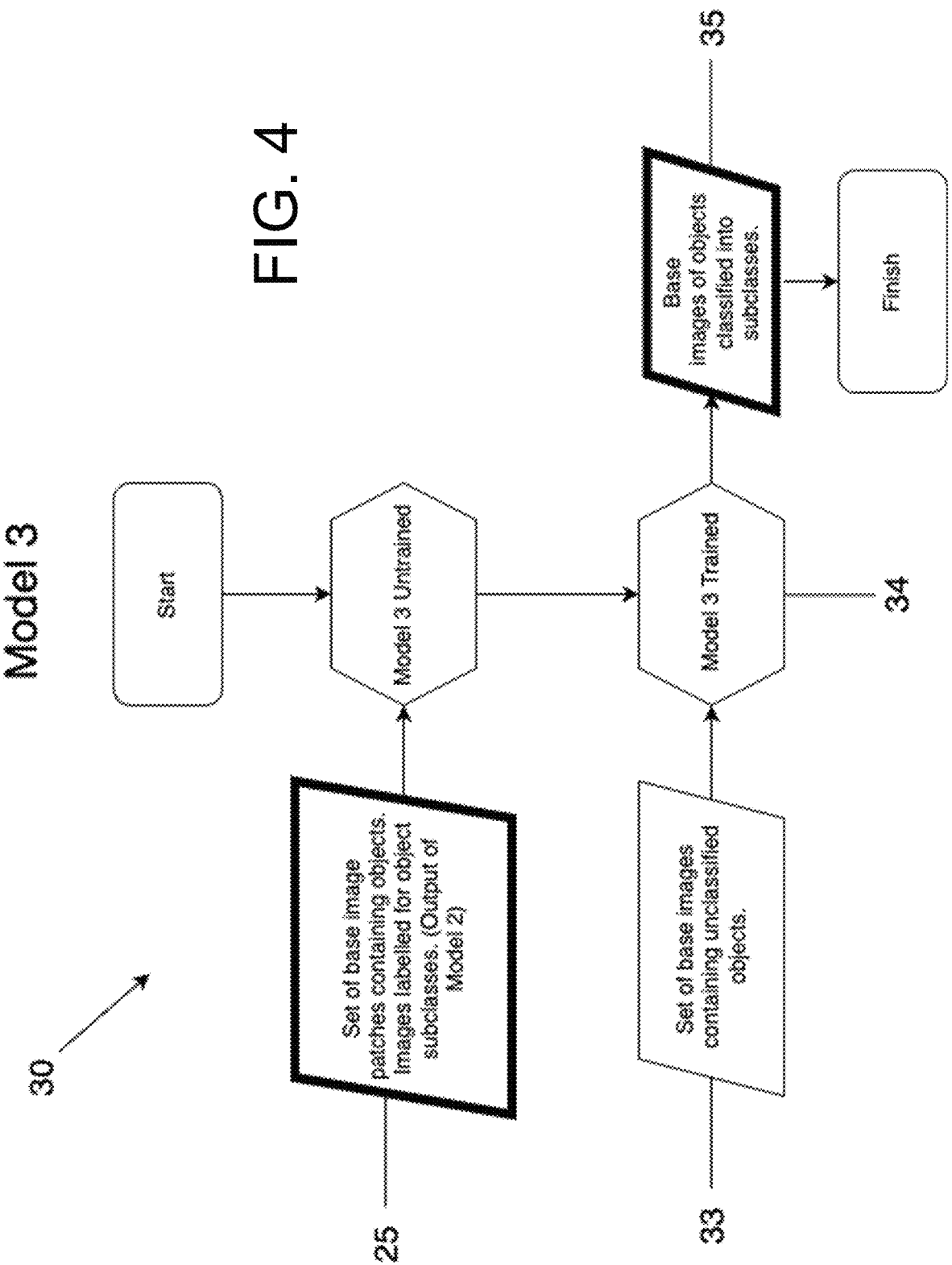
FIG. 4 shows a flow diagram describing the workflow for Model 3, in
accordance with disclosed embodiments.

FIG. 4 shows a flow diagram describing the workflow for Model 3 30. The same principles defined for the previous flow-diagram symbols apply.

Figure 5:
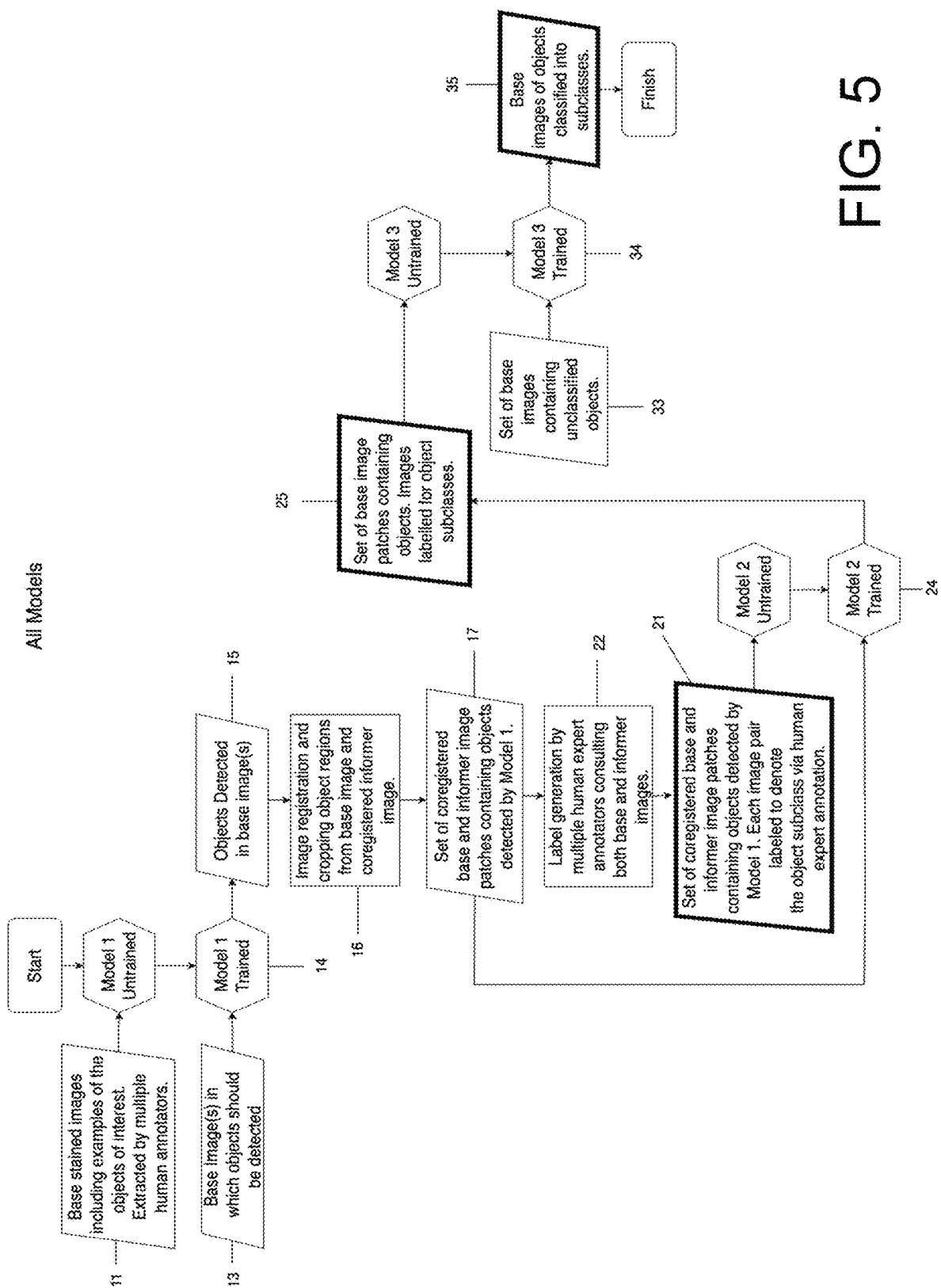
FIG. 5 shows a flow diagram showing the interrelation of workflows for Models 1, 2, and 3, in accordance with disclosed embodiments.

FIG. 5 shows a flow diagram showing interrelation of workflows for Models 1 10, 2 20 and 3 30. The same principles defined for the symbols in the previous flow diagrams apply.

1.1.2 System

Figure 6:
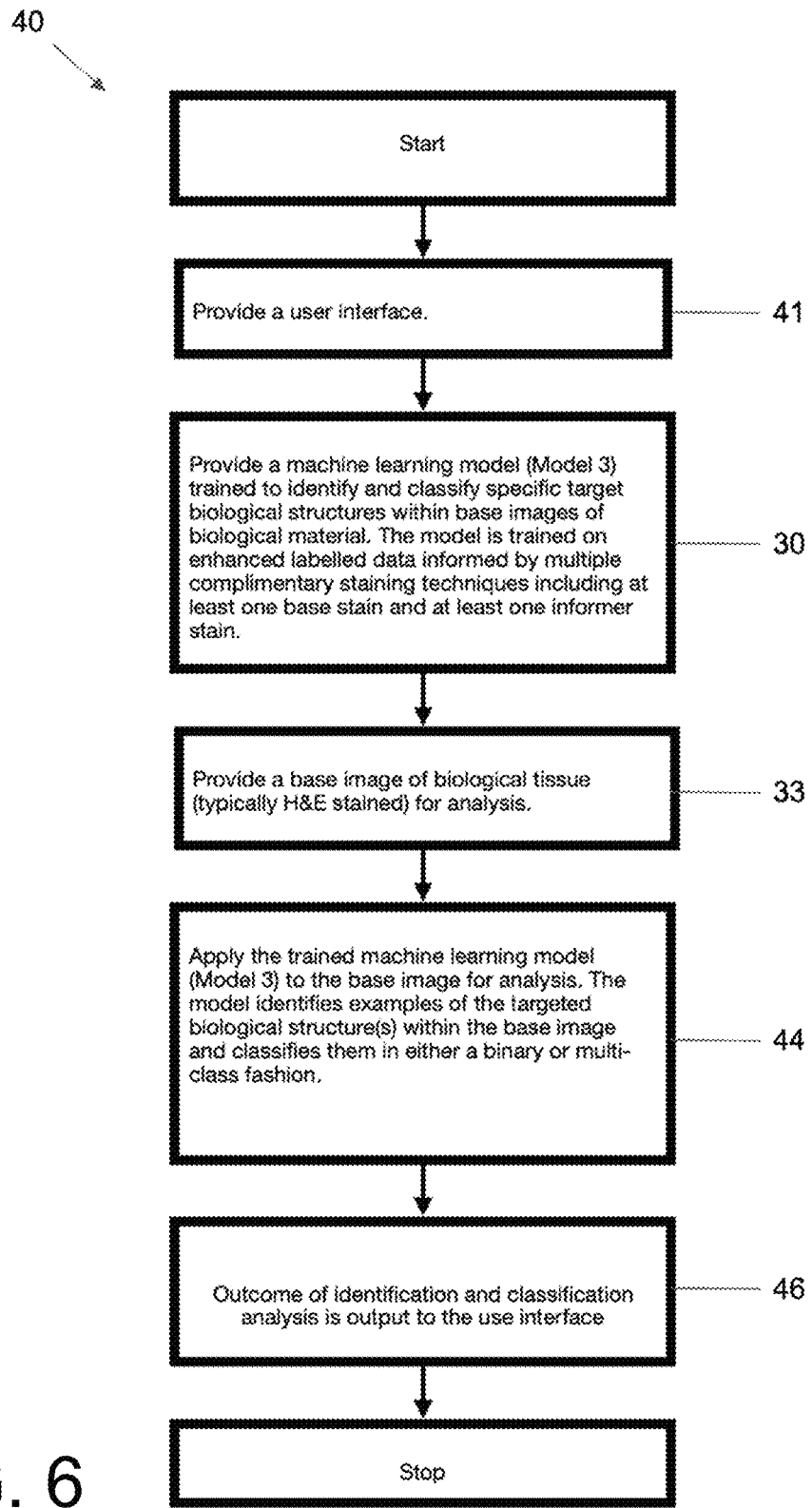
FIG. 6 shows an example workflow of the system, in accordance with disclosed embodiments.

The disclosed embodiments include a stable operational system 40 for performing digital pathology tasks. The central functionality of the system 40 is provided by a trained machine learning model 30 (Model 3) which was created according to the steps described in Method a) (including Model 1 10 and optionally Model 2 20). The completed system 40 functions to identify, or identify and classify, objects of interest (e.g. types of cell) within base images 33 (typically digital microscope images of H&E stained biological tissue) alone with high accuracy and a high processing rate. By modifying the exact process used to produce it, the system 40 can be recreated to perform a multitude of common tasks within the pathology sector with improved performance as compared with individual human pathologists or other automated methods. The completed system 40 accepts a single type of input of base images 33 (typically tissue slides stained with the common H&E histological staining designed to reveal the structure). It identifies and classifies 44 the cases of the object of interest for which it has been trained within the input base image 33. A diagram of the workflow of the system 40 described in (a) is shown in FIG. 6. It describes how the system 40 is implemented for carrying out identification and classification tasks.

Figure 7:
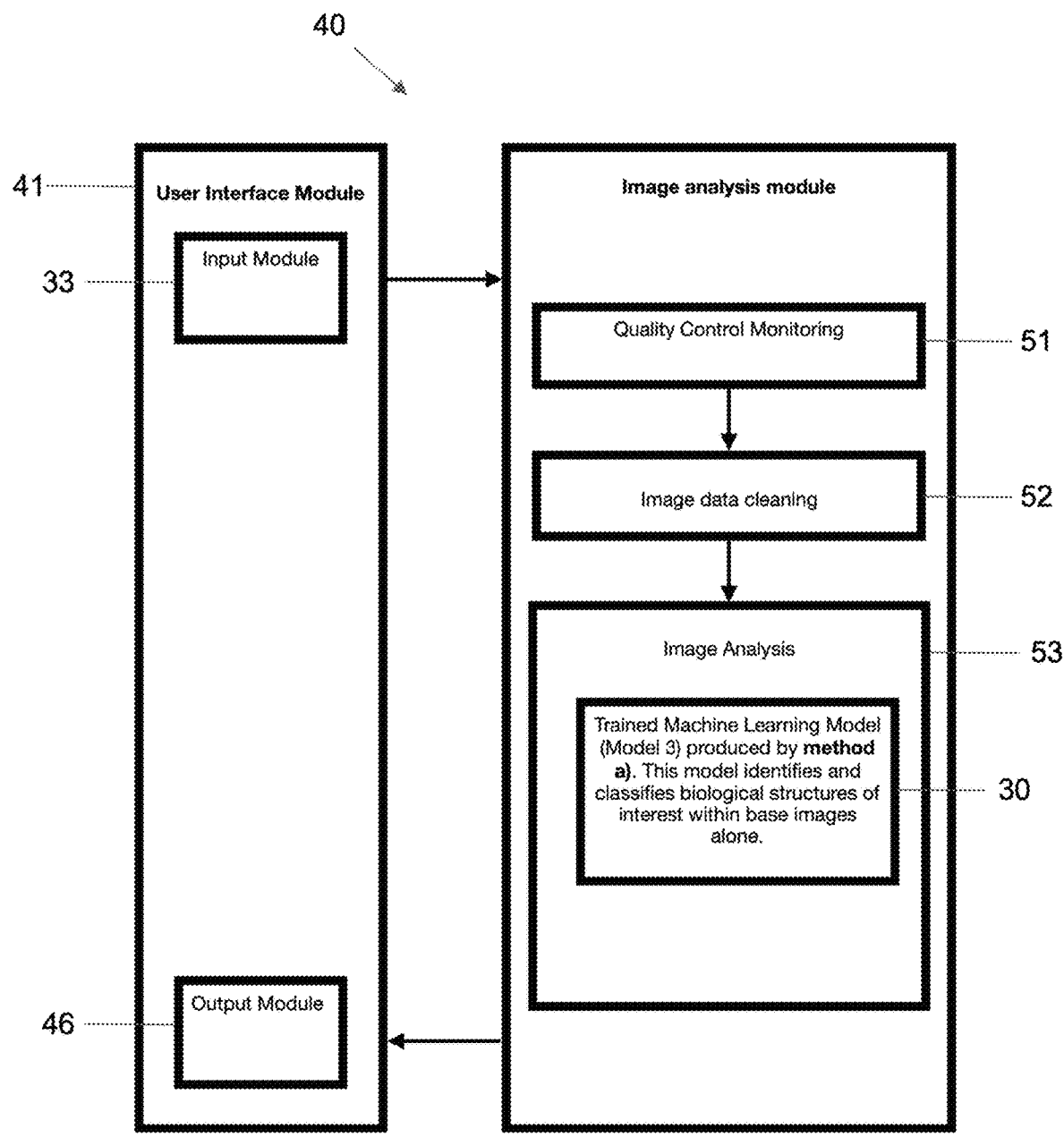
FIG. 7 shows an example of a system diagram for object identification and classification in base images, in accordance with disclosed embodiments.

The system 40 is computer-based. It accepts digital microscope images of biological tissue (base images 33) through a user interface 41, analyzes 53 them using a trained machine learning model 34 (developed using the steps described in method a)), and then outputs 46 the results of the object identification, classification or other analysis through the user interface 41. The system 40 incorporates machine learning models trained using Informer Image(s) 6 for enhanced label extraction for biological structures of interest within coregistered base images 17 using the method a) disclosed in this document for enhanced accuracy and efficiency. The system 40 also includes data pre-processing modules for quality control 51 and data cleaning 52. The diagrams in FIG. 6 and FIG. 7 are intended to better elucidate the system which we define. FIG. 7 shows a sketch of the system diagram for object identification and classification in base images.

1.2 Brief Summary of b)

This part of the disclosure describes in more detail the different potential methods for automated label extraction (object class extraction) from coregistered base and informer images 17 of the same biological material. The methods summarized here are examples of suitable tools to fulfill the automation of step vi) in method a). However, the methods listed here do not form an exhaustive list of all of the automation methods which could be used.

Automated label extraction always relies on the establishment of rules for differentiating between the different classes to be labeled.

We disclose two key methods for establishing these rules for automated label extraction:
- Those which implement automatic learning of the rules via machine learning models
- Those implementing rule-based label extraction (rules derived by a human expert but automatically applied)

This technology disclosure covers both of these possibilities for the automation of label extraction for use in method a).

Regardless of whether the rules are automatically learned, or manually derived and then automatically applied, the precise workflow required will depend upon the type of informer image(s) 6 being used. The specific requirements for automated label extraction when using immunohistochemistry- and mIF-stained digital microscope images as Informer Image(s) 6 to complement H&E stained base images 3 are described in sections 2.1.6 and 3.2.2.4 respectively. Other types of informer stainings may have their own unique requirements.

The methods summarized here in b) can be considered as interchangeable plug-ins for inclusion in the workflow of the method in a). Both of the approaches described in sections 1.2.1 and 1.2.2 therefore require as a precursor that all of the steps described in method a) up to the end of step v) have already been successfully completed before they can be undertaken.

By automating step vi) in method a) using the methods described in b), less human expert time is required and the overall accuracy and through-put of the process is significantly increased. The labels produced by the machine learning based label extraction approach are of superior accuracy compared to those produced by either rule-base label extraction or manual label generation. We do not however limit ourselves to machine learning based label extraction, and include rule-base label extraction and manual label extraction alternatives in this disclosure too.

A brief high-level overview of label extraction via machine learning based and rule-based techniques follows:

1.2.1 Machine Learning Based Label Extraction

This approach to label extraction implements the machine learning model, Model 2 20, as described in section 1.1.1 to realize the extraction of labels from an input of stacked base and informer images 17 of the biological structures of interest. This method produces superior label data as compared with the rule-based label extraction technique, or manually generated labels based on both base 3 and informer 6 images.

Machine learning based label extraction utilizes machine learning models trained on annotations which are manually produced by multiple human experts 22 using informer images 6 in addition to base images 3 of the objects of interest. This means that the human expert examines not only the base image 3, but also the coregistered informer image(s) 6 to aid their annotations. By including multiple human expert annotators in the creation of the training data 21 for the model 20, the impact of individual biases and errors on the final trained model 24 can be reduced. A machine learning model (e.g., a convolutional neural network, a transformer, or another suitable architecture) can be trained on the dataset of labeled images generated by the human expert annotators 21.

Supervised machine learning based label extraction models can make use of the annotations produced by experts and both the base image 3 and coregistered informer image(s) 6 in the training phase. The base image 3 and informer image(s) 6 can be stacked 16 and then input to the model architecture to produce an output probability that the cell belongs to one class of biological structure of interest or not. A loss (or error) can be computed for the object using human expert annotations created using the additional information offered by the informer image(s). Parameters of the model 20 can be optimized to minimize the loss in the training phase, e.g., to produce the same outputs as the pathologist annotations.

The trained label extraction model 24 receives as input stacked base and informer image patches 17 (or in some cases the Informer Image(s) image alone) of the biological structures of interest. As an output 25 it predicts the probability of the object of interest belonging to a given class. Binary or multiclass models can be used depending on the precise requirements of the application.

1.2.2 Rule Based Label Extraction

If this approach to label extraction is implemented, it replaces Model 2 20 in the workflow described in section 1.1.1.1. In this workflow arrangement only Model 1 10 and Model 3 30 will remain in the workflow.

To achieve this method for automated label extraction, rules are manually derived for each class of object to be classified. The rules are used to automatically extract information held within the informer image(s) (and potentially also the coregistered base image in parallel), which is then used to label the corresponding structures of interest already identified in the coregistered base image(s) 17 during method a) step v).

i) Rule Creation

Rule creation can be based on parameters-of-interest which are manually identified and then extracted from a representative sample of coregistered base images and informer image(s) 17 of the biological structure of interest. These features could, for instance, be: cell nucleus size, intensity of the staining as computed from the color-deconvoluted image at specific locations in the biological structure, or many other possibilities.

Once the parameter-of-interest has been computed for each biological structure of interest (and other objects which we wish to discern against), human expert (pathologist or other trained expert) analysis is manually applied to find separations between the biological structures of interest and other types of structure present.

The human expert analysis identifies the threshold-value or value-range for the parameter-of-interest by which the particular class of biological structure may be identified.

Multiple parameters-of-interest may be combined to form a rule to isolate a particular class of object that is very effective.

The complexity of the rules required to extract labels of high quality varies between the type of informer image(s) used, and the type of biological structure which is being targeted for classification.

ii) Rule Application

When rules for every class of biological structure of interest have been derived, they can be used to automatically extract labels from the informer image(s) for the objects already identified within the base image(s). Just as for machine learning based label extraction, the labeled images output by the rule-based label extraction technique can be used as the training data for Model 3 30 as described in section 1.1.1.

The precise application of a rule can be dependent on the way that rule was derived. Rules based on thresholds for parameters of interest are applied by computing the parameter for a given image of a cell in IHC and applying the precomputed threshold. More complex rules that were derived based on learning algorithms (decision trees or other) are applied by computing all relevant parameters of interest for a given image of a cell and then applying the respective precomputed thresholds or projections (performing "inference" of the learning model). This technology disclosure covers both possibilities.

2. Immunohistochemistry (IHC) Work-flow

This section discloses the technology described at a high-level in section 1 from the more detailed perspective of its embodiment (implementation) for use with one or more IHC stainings as informer image(s) 6 to complement the information contained within base (typically H&E stained) images 3. Section 3 then documents the deviations from the IHC workflow which are required in order to perform the same high-level processes described in section 1 using multiplex immunofluorescence stainings as the informer images 6 to be combined with the base (typically H&E stained) image(s) 3.

2.1 Technical Summary of Method 2.1.1 Overview

In some embodiments, the inputs can be multiple digital microscope images of the same biological material obtained under different histological stainings. This section describes the case where the base image 3 (typically an H&E stain) is complemented by one or more additional subsequent image(s) of the same tissue 1 acquired under IHC staining to provide the informer image(s) 6.

Information on the implementation of method b) for automated label extraction from IHC stained Informer Image(s) is supplied in section 2.1.6.

2.1.2 Staining Process and Image Acquisition for IHC Workflow

The base stain of the slide can be done first, (H&E is most commonly used for the base stain, but other stainings could also be used) and then a whole-slide digital microscope image is recorded 2. The base stain can then be removed 4 using a suitable agent (hydrochloric acid or other). After removing the base stain, one or more secondary IHC stainings can be applied and for each a whole slide digital microscope image can be recorded 5. These IHC stained images can act as the informer images 6 to offer additional information suitable for reducing ambiguity in the analysis of the initial base (H&E) stain.

Consistent with disclosed embodiments, the base (H&E) stain can be applied first and the base image obtained 2. The IHC stain can be applied after, and the informer image(s) subsequently obtained 5. This ordering can ensure that the quality of the base (H&E) stained images used for training the machine model matches the quality of those images 33 that the final classifier 30 will be applied to. Differences between the image qualities can reduce the performance of the final classifier 30.

The IHC stained informer images 6 can provide additional information to remove ambiguity and risk from the identification of biological structures as compared with a single H&E stain. The informer IHC stain can be used for the generation of labeled training data to guide cell detection and classification models for application on the base (typically H&E) stained images. The IHC data can replace (or improve on) the labor-intensive and human-error prone process of manual annotation of slides by trained pathologists (as described in the background section) for providing labeled input for the training of machine learning models for the recognition of biological structures in digital microscope images of biological material.

2.1.3 Quality Control

Quality control represents an optional but powerful component of the workflow. The specific tasks and processes included in this step can vary depending on the specific use case. In general, the goal here is to give an overview of some of the possible tools which have already been developed. These are listed below, but the list is not exhaustive, and merely intended to give an impression of the types of additional proprietary tools which may be incorporated into this step of the work-flow:

Quality control processes and tools may be applied to both the base image 3 (H&E) and informer image(s) 6 (IHC stained).

For clarification, the techniques described below for IHC may also be applied in the mIF process described in section 3. However specific techniques may not always be applicable in all cases, and thus should be assessed on an individual basis.

2.1.3.1 Removal of Necrotic Tissue

Regions of necrotic tissue within images can create false results and distortions if they are included in the later analysis stages of the disclosed workflow. For these reasons it can be advantageous to identify and remove these regions from the images before further processing and analysis occurs.

A suitable deep-learning based machine learning algorithm can be implemented for segmentation of regions of necrotic tissue from other tissue regions. The algorithm can be based on a machine learning model trained on annotations generated by qualified experts (pathologists or similar). The algorithm can function to identify and discard sections of the whole slide image containing necrotic tissue.

2.1.3.2 Removal of Anthracosis Pigment

An additional source of label noise comes from anthracosis, an accumulation of black carbon pigment in lung tissue. This is problematic because it is present in both the H&E base and IHC informer images and can be mistaken for IHC signal by our label extraction approach. This then leads to false results and distortions which impact the quality of the analysis. To address this issue we have developed a cell-level filter which identifies and removes any anthracosis deposits which are falsely picked up by the cell detection algorithm.

2.1.3.3 IHC Image Normalization

Variation in DAB (diaminobenzidine, an IHC stain) intensity across different slides of the same stain are often noticed during quality control observation (after the generation of the images). Similar variations are possible for many other types of histological stain which would be valid to implement within the method and system described in this technical disclosure.

This variation in staining intensity has the potential to induce label noise, particularly when rule-based label extraction is implemented. To standardize the IHC stainings, Reinhard normalization (described in next paragraph) can be used, however other approaches are also technically valid to achieve the same result. Whatever approach to stain normalization is adopted, the result is that slides with differing stain intensities within each group are normalized to match their respective "source" slide.

Reinhard normalization is a technique that maps the color distribution of over-or under-stained target images to that of a well-stained source image. This is done by use of a linear transform in a perceptual color space. In essence, Reinhard normalization is a technique which employs statistical analysis to transfer one image's color characteristics to another. It can be used to achieve a color correction by choosing an appropriate source image and applying its characteristics to another target image.

2.1.3.4 False IHC Staining

Detection and removal of regions where there is false staining in the IHC stained image. False staining can occur when biological structures are destroyed and/or altered and the resulting biomass binds to the chosen biomarkers. For example, regions at the border of the section can exhibit false staining due to damage sustained during sectioning. This type of damaged tissue can be removed by excluding a border region of the tissue from the subsequent analysis.

2.1.3.5 Damage from Tissue Slicing

The process of slicing the tissue for slide preparation can damage cells and impact on the quality of the stain. This problem can manifest particularly strongly at the edges of the tissue. For this reason, quality control tools were developed which identify and discard all material which is within a set distance of the tissue border.

2.1.3.6 Tissue Repositioning During Stain Removal and Restaining

An additional source of unusable image regions arises when the tissue is occasionally damaged/moved during processing of the second staining step (removal of one stain 4 and restaining with a new stain 5). Thus the IHC scan must also be quality controlled for regions where this has occurred.

2.1.4 Coregistration and Alignment Masks

This step of the process overlays and aligns the base image(s) and informer image(s) with a high degree of accuracy. For all embodiments of the method, the ordering of the image coregistration and object detection steps is interchangeable. Thus, the ordering of steps 2.1.4 and 2.1.5 can be swapped without any impact on the workflow.

2.1.5 Detection of Specific Biological Structures within the Base (H&E Stained) Image Biological structures which are the target of the analysis are identified within the base image 13. Examples of possible targets include cells, vessels, glands, glomeruli or regions of necrosis. However, the approach described here is not limited to these examples.

Detection of these biological structures of interest can be done via either:

Automated approaches using machine learning models (Model 1 10 from section 1.1.1.2) (approach with optimal results and output quantity)

Human annotation

When examples of the target biological structure are identified 15 within the base image 13, a patch containing the structure(s) is cropped 16 from the base (typically H&E stained images) and the equivalent region is also cropped 16 from the coregistered informer (IHC image). These cropped coregistered images are compiled into a dataset 17 representing many (potentially millions) of examples of the detected objects of interest. Examples of the types of coregistered H&E and IHC stained images 17 which are produced by this process are shown in FIGS. 8 and 9.

Figure 8:
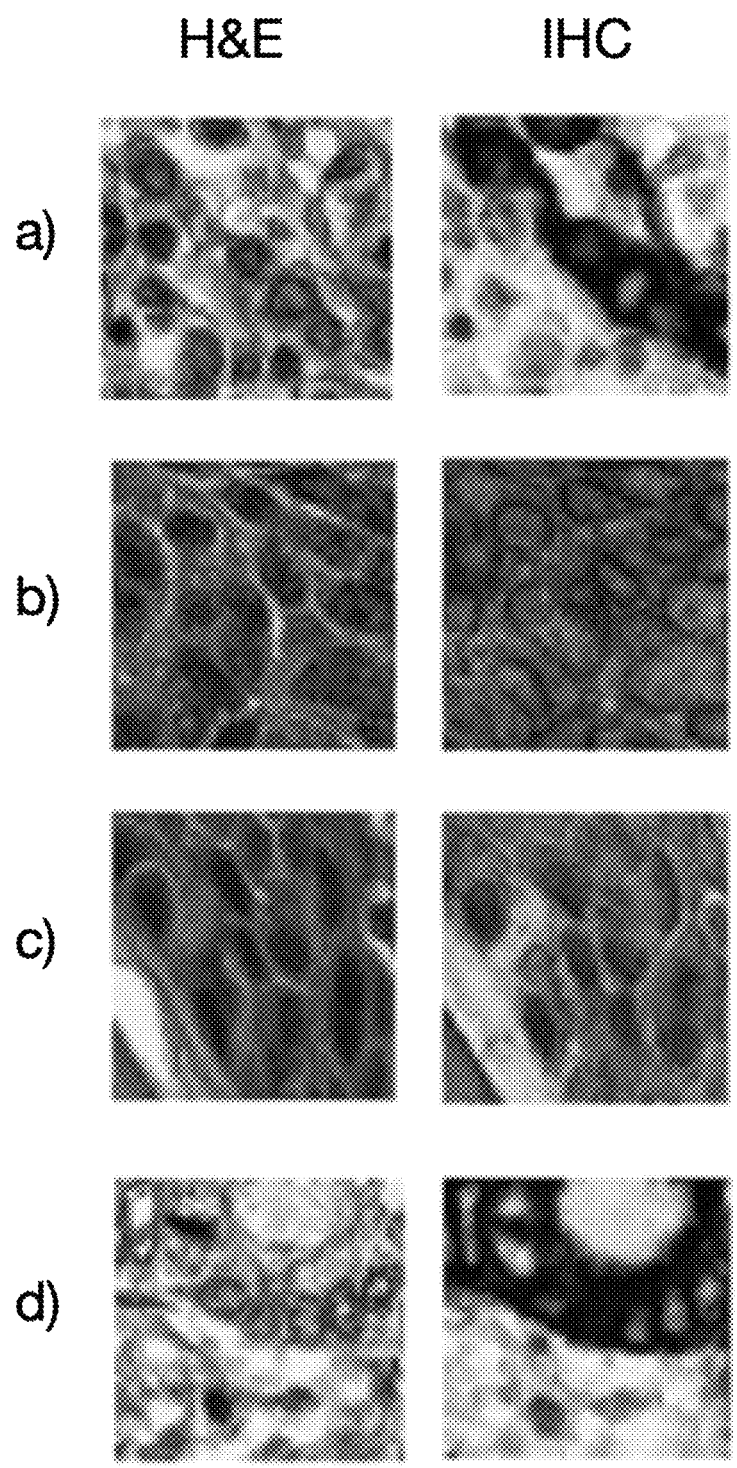
FIG. 8a shows an example of a coregistered cropped image patch pair of the same tissue region under H&E staining (left) and IHC staining (right), in accordance with disclosed embodiments.
FIG. 8b shows an example of a coregistered cropped image patch pair of the same tissue region under H&E staining (left) and IHC staining (right), in accordance with disclosed embodiments.
FIG. 8c shows an example of a coregistered cropped image patch pair of the same tissue region under H&E staining (left) and IHC staining (right), in accordance with disclosed embodiments.
FIG. 8d shows an example of a coregistered cropped image patch pair of the same tissue region under H&E staining (left) and IHC staining (right), in accordance with disclosed embodiments.

In FIG. 8, each row (a to d) is an example of a coregistered cropped image patch pair 17 of the same tissue region under H&E stain (left column) and IHC staining (right column). In each case the region was labeled as containing carcinoma cells (specifically the carcinoma cells are forms of non-small cell lung cancer). The tissue shown in FIGS. 8a to 8d is lung tissue and a CK-KL1 IHC stain was used. However, this disclosure is not limited to only this combination of tissue and staining, and any combination of tissue and staining is suitable for use in the systems and methods disclosed herein.

Figure 9:
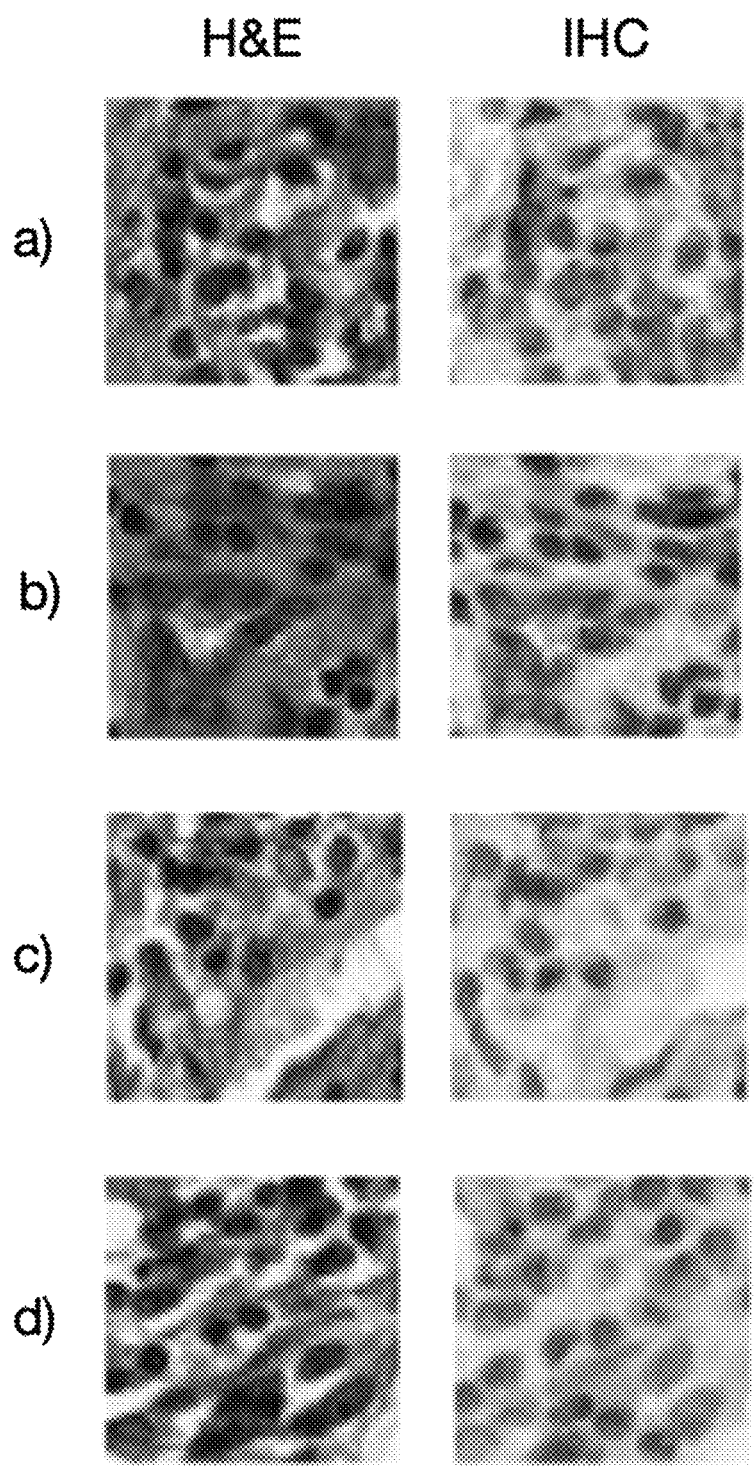
FIG. 9a shows an example of a coregistered cropped image patch pair of the
same tissue region under H&E stain (left) and IHC staining (right), in accordance with disclosed embodiments.
FIG. 9b shows an example of a coregistered cropped image patch pair of the same tissue region under H&E stain (left) and IHC staining (right), in accordance with disclosed embodiments.
FIG. 9c shows an example of a coregistered cropped image patch pair of the same tissue region under H&E stain (left) and IHC staining (right), in accordance with disclosed embodiments.
FIG. 9d shows an example of a coregistered cropped image patch pair of the same tissue region under H&E stain (left) and IHC staining (right), in accordance with disclosed embodiments.

In FIG. 9, each row (a to d) is an example of a coregistered cropped image patch pair 17 of the same tissue region under H&E stain (left column) and IHC staining (right column). In each case the region was labeled as not containing carcinoma cells. The tissue shown in FIGS. 9a to 9d is lung tissue and a CK-KL1 IHC stain was used. However, this disclosure is not limited to only this combination of tissue and staining, and any combination of tissue and staining is suitable for use in the systems and methods disclosed herein.

Note with regard to automated machine learning approaches to object identification: Many types of machine learning model can be used to accomplish the described object identification process. We do not describe a specific method in detail here as the disclosure is intended to cover all machine learning approaches and architectures which could potentially be used to complete the task.

2.1.6 Label Extraction from the IHC Stained Informer Images

The purpose of the coregistered IHC stained informer image(s) 17 is to derive additional information on each structure identified within the base image 3 as described in section 2.1.5. When this process is done automatically by a machine learning model, this is Model 2 20 from section 1.1.2. The information is used to provide labels for the identified structures to facilitate their use in the later training of machine learning model based classifiers (Model 3 30).

The extraction of this complementary information from the coregistered IHC informer image(s) 17 is to provide additional labels to the biological structures identified in the base H&E stained image may be achieved in one of the following ways:

By automated machine-learning based label extraction (see section 1.2.1) (Model 2 20 from section 1.1.1.2)

By automated rule-based label extraction (see section 1.2.2) (substitutes for Model 2 20 in workflow)

By human expert annotations (substitutes for Model 2 20 in workflow)

All three label extraction methods have been successfully demonstrated for inclusion in the IHC workflow disclosed here. Examples of labeled image patch pairs 17 (H&E and IHC) are shown in FIGS. 8 and 9. All of the image patch pairs in FIG. 8 were labeled as containing carcinoma cells by the label extraction process. All of the image patch pairs contained in FIG. 9 were labeled as not containing carcinoma cells by the label extraction process.

The IHC based embodiment of the technology has also been demonstrated as being effective when both the IHC and base image are included as input 17 into Model 2 20, and also when the IHC image alone is used as the Model 2 20 input. A slight improvement in the quality of the label generation is typically noted when both IHC and base images are used, however both variants of the technology are valid and included in this disclosure.

The extracted labeling information can later be used to generate training data for machine learning models. Once trained, the machine learning models will be able to detect and classify the objects of interest within purely base stained images with exceptional accuracy.

2.1.7 Model Development and Training

This step of the process implements the labeled data sets 25 produced in the earlier steps to train a machine learning model 30 (Model 3 30 from section 1.1.1.2) for use as a system 40 for the identification and classification of the biological structures of interest. The type and architecture of Model 3 30 can vary dramatically depending on the specific application for which it is designed. Examples include, but are not limited to, VGG16, ResNets such as ResNet18 or ResNet50, or Visions Transformers.

After successful label extraction from the IHC stained informer image(s) and coregistered base images 17, labeled training data sets 25 are ready for use in training machine learning models for identification and classification.

Many IHC stainings produce binary labels, although in some cases the labeling can be categorical. For the case of binary labels for the targeted biological structures (e.g.: Plasma cell vs. Non-plasma cell), multiple binary labels can be combined to build more complex multi-class models in various ways.

The classification training pipeline trains the machine learning model 30 (Model 3) developed for a specific application using the labeled image patch dataset(s) 25 created in sections 2.1.5 and 2.1.6.

2.2 Technical Summary of System

After completing all of the steps in the method described in section 2.1, the result is a trained machine learning model 34 (Model 3 30) suitable for identifying and classifying biological structures of interest within base stained digital microscope images 33 of biological tissue.

Figure 10:
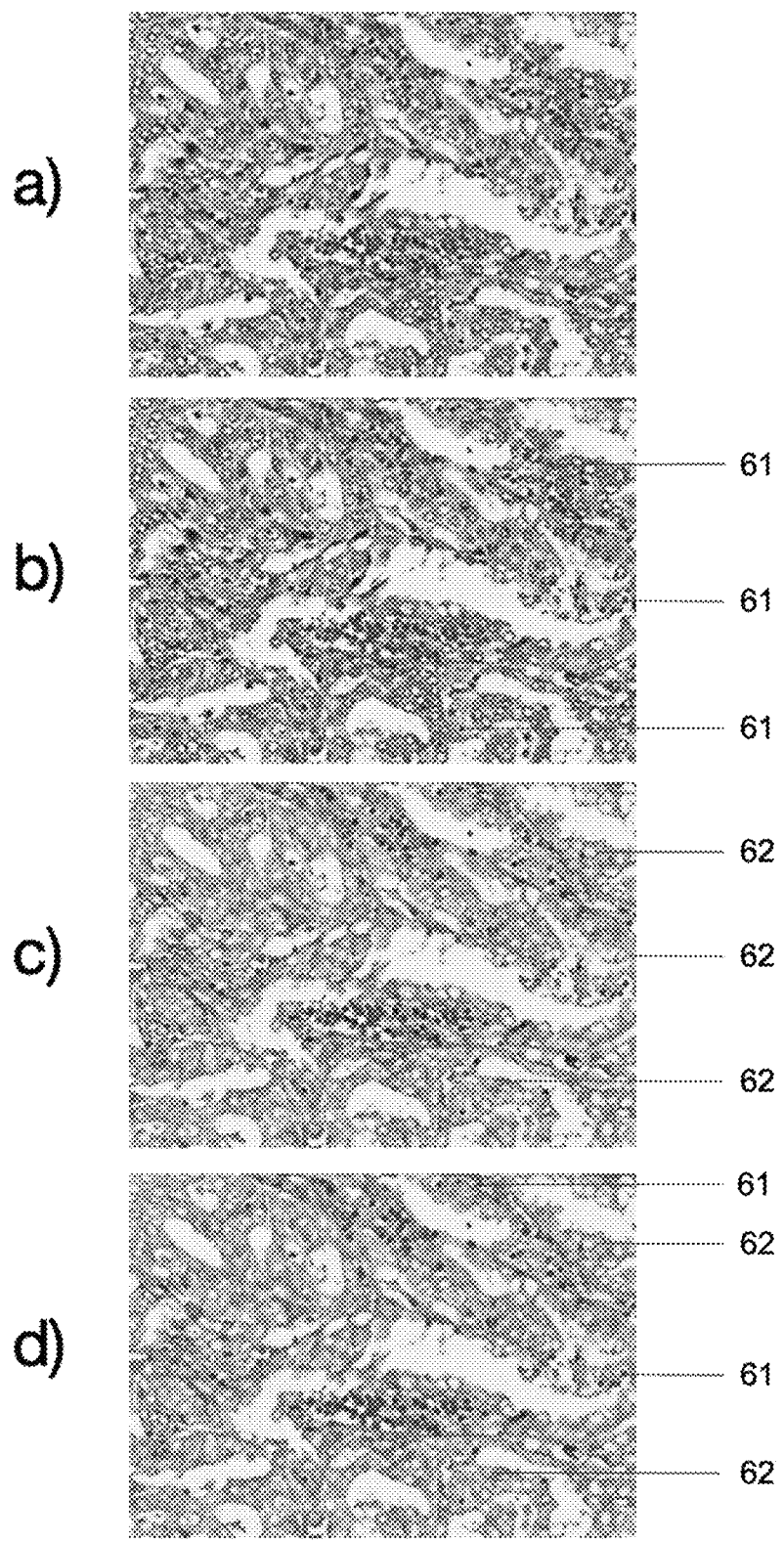
FIG. 10a shows an output image from one example of a user interface developed for use in the system, where the output image shows the original digital microscope image of a region of the H&E stained tissue, in accordance with disclosed embodiments.
FIG. 10b shows an output image from one example of a user interface developed for use in the system, where the output image shows red polygons overlaid on the original image highlighting the locations in the image where cases of "Immune cell-lymphocyte" classified images were detected, in accordance with disclosed embodiments.
FIG. 10c shows an output image from one example of a user interface developed for use in the system, where the output image shows yellow polygons overlaid on the original image highlighting the locations in the image where cases of "No immune cell-lymphocyte" classified images were detected, in accordance with disclosed embodiments.
FIG. 10d shows an output image from one example of a user interface developed for use in the system, where the output image displays both the overlaid red polygons and the overlaid yellow polygons simultaneously, in accordance with disclosed embodiments.

The trained machine learning model 34 can then be implemented within a system 40 for identification and classification as described in section 1.1.2. The system 40 accepts individual base (H&E) stained images 33 of tissue as input, and identifies and classifies 44 objects of interest within them. The system 40 can produce highly accurate results due to training using training data that is of high quality. The inclusion of the additional information offered by the IHC stained image(s) in addition to the H&E stained base image 3 in the label generation process can enable creation of this high-quality training data. The system 40 outputs the results 46 of the analysis through a suitable user interface 41 for visualization. Images of results displayed in one example of a realization of this type of user interface 41 are shown in FIG. 10. Many other approaches to the design of the user interface and results presentation are possible and valid for us in conjunction with the disclosed system.

FIG. 10 shows output images 46 from one example of a user interface 41 developed for use in the system 40 described in section 1.1.2 (which implements the trained Model 3 30). In this example IHC enhanced label extraction was used to inform the generation of labels of "immune cell-lymphocyte" or "non-immune cell-lymphocyte" for candidate objects. The results 46 are displayed in the user display 41 using various overlays of the original H&E stained digital microscope image 33. a) shows the original digital microscope image 33 of a region of the H&E stained tissue. b) shows red polygons 61 overlaid on the original image 33 highlighting the locations in the image where cases of "Immune cell-lymphocyte" classified images were detected. c) shows yellow polygons 62 overlaid on the original image 33 highlighting the locations in the image where cases of "No immune cell-lymphocyte" classified images were detected. d) displays the results overlays b) and c) simultaneously.

3. Multiplex Immunofluorescence (mIF)

3.1 Overview and Background

Immunofluorescence is a common technique based on specific antibodies which are conjugated to fluorescent dyes. These labeled antibodies bind directly or indirectly to targets within the biological material being studied. The sample being studied is then exposed to short-wavelength, high-energy light, which is absorbed by the dye and emitted at a different wavelength. This fluorescence emitted by the dye can be collected by microscope equipment for imaging and analysis.

Multiplex immunofluorescence (mIF) allows the simultaneous detection of multiple antibodies (each conjugated to a different fluorescent dye which emits light at a different wavelength) on a single sample of biological material for microscopic analysis. IHC is typically limited to staining for a single biomarker (although Multiplex Chromogenic Immunohistochemistry variants exist). mIF, however, facilitates simultaneous antibody-based detection and quantification of multiple targets, plus a nuclear counterstain (for example DAPI), on a single tissue section.

By combining the results of the different antibody stainings in mIF, vastly more detailed information can be gathered than would be possible for a single antibody staining technique.

Like IHC, mIF stainings can be implemented in the methods and system described in section 1 of this document. The mIF images are used as informer images 6 within the methods and system described. The workflow combines coregistered base (H&E stained) and informer images (mIF stained) 17 digital microscope images of the same biological material to create labeled base image datasets 25 (using Model 2 20 or alternative). These labeled base images 25 (labeled with high accuracy) are subsequently used to facilitate the training of the machine learning model (Model 3 30) for the highly accurate extraction and classification (labeling) of target biological structures from the base H&E stained images alone). Section 3.2 of this document focuses on this.

3.2 mIF Informed Label Extraction for Developing Machine Learning Models for Application on H&E Stained Images 3.2.1 Brief Overview of this Embodiment of the Technology, and the Gap It Aims to Fill Very similar overall goal to IHC process described in section 2. However, the specifics of the workflow differ due to the specific nature of the mIF stainings which are used in this technique to fulfill the role of the informer image(s) 6.

A generalized description is as follows:

Acquisition of multiple microscope images of the same biological tissue 1 under different stainings (at least one base stain 3 (typically H&E) and at least one informer image 6 (mIF, DAPI or other stainings may additionally be used). The workflow for mIF image acquisition can differ from that for IHC. mIF stainings can be carried out first, and the H&E base stain done afterwards. The order can also be reversed, with H&E staining done first, and the mIF stains done afterwards. This contrasts with the strict ordering requirement of the IHC workflow where only the H&E base stain can be first and the IHC stain second. In addition, when the mIF stain is applied first, there is no requirement to apply a stain removal process 4 before the later application of a base H&E stain. The mIF stains present in the tissue do not significantly disrupt the quality of the H&E stain and image generation 2. Technical limitations resulting from the specific nature of the stainings used dictate which of the stainings should be performed first to achieve results of sufficient quality to be implemented in the broader workflow.

Coregistration 16 of the images (as previously mentioned in section 1.1.1.1, the ordering of this step and the following step (3) is interchangeable without impacting on the outcome of the method).

Detection 15 of target biological structures within the base (typically H&E) image(s) 13 using a machine learning model 10 (Model 1 10) (e.g. DAPI-based nucleus detection model if DAPI has been used).

Extraction of classifier labels for the biological structures identified in 3) based on the analysis of the additional information contained within the coregistered mIF stained Informer Image(s) 6. When done via a machine learning based label extraction approach this is Model 2 20.

Training of a machine learning model (Model 3 30) based on the labeled dataset 25 produced in step 4. The trained Model 3 34 enables highly efficient and accurate identification and classification and subsequent analysis of the target biological structures within base stained (typically H&E) images 33 of biological material only.

Quantification and spatial analysis of the biological structures of interest within previously unseen base stained digital images 33 using the trained machine learning model 34(Model 3 30) developed throughout steps 1) to 5).

3.2.2 Technical Summary

To achieve the workflow described in section 3.2.1, the steps described in the following subsections are required. In general, a similar workflow to the IHC version is required. Some key technical differences are required due to the differing nature of the stainings used:

3.2.2.1 Staining of Biological Samples for Microscopic Analysis and Image Acquisition Many different types of mIF staining can be used as the input to the technique (e.g. varying numbers of stains, different staining types and other variations.) For example, a 12 stain mIF process can be used. Such a 12-plex mIF could involve each sample being stained with three rounds of mIF (each round consists of four antibodies+DAPI) (images recorded at the completion of each staining round for the four antibodies just stained). Many other approaches could also be implemented with the inclusion of minor adjustments to the overall mIF workflow.

3.2.2.2 Image Coregistration

Here we briefly describe a coregistration method 7 suitable for mIF image sets comprising multiple subgroups. Each subgroup contains multiple immunofluorescence stained images (e.g. four), with a single DAPI image also included in each subgroup. Other registration techniques are applicable for differently structured mIF data (for example produced via different protocols). The appropriate registration technique for the particular type of mIF data can be inserted into this step of the process as required.

For the mIF data structure detailed above:

Due to the large number of images acquired, and the limited structural information contained in individual mIF images, the DAPI stained image from each subgroup of four mIF stainings can be used as the basis of coregistration of all of the 12 images from the three rounds of mIF. The base (H&E) stained image is also coregistered to each mIF set based on the DAPI images.

DAPI-DAPI

HE-DAPI 3.2.2.3 Object (e.g. Cell) Detection

Similar to the IHC process previously described: A machine learning model 10 (Model 1 10) can be applied to detect the biological structures of interest within either the base (H&E) or DAPI stained images (different tools available for each).

3.2.2.4 Label Extraction

Similar to the IHC process previously described: The mIF images can be used as informer image(s) 6 to provide information to improve the label extraction process for each of the targeted biological structures identified in step 3.2.2.3.

Label extraction can be performed by a machine learning model 20 (Model 2 20). In the absence of sufficient human expert annotator- or time resources to create training data, automated rule-based label extraction has also been demonstrated to be effective (and is not dependent on obtaining large numbers of manually generated human expert annotations). Labels denoting specific subclasses can be allocated to each of the objects previously identified in step 3.2.2.3. The result can be a data set of labeled base images of the objects with labels denoting the subclass. This forms a training data set 25 for use in training a classifier to act on base stained images 33 of objects alone (Model 3 30) that is of a high quality due to the accuracy of the labeling of the base images of the objects.

3.2.2.5 Training of Machine Learning Models

The labeled data set developed through steps 3.2.2.1 to 3.2.2.4 can be used to train a machine learning model 30 (Model 3 30) for highly accurate identification and classification of biological structures of interest within simple H&E stained microscope images of biological material (base images 33) only. Due to inclusion of the mIF data in the label generation process for the training data, the results produced are more accurate than could be achieved if the label generation was done using the base images alone as input.

The trained model 34 can be incorporated into a similar system to the one described in section 2.2. The system is again a highly efficient and accurate identifier and classifier which can operate purely on comparatively cheap and accessible base images, without the need to acquire mIF images for every sample.

The high-level work-flow for mIF is identical to the one described in FIG. 5. The system built based on this workflow for the characterization of H&E stained slides can be identical in fundamental structure and functionality to the one built via the IHC approach.

3.2.3 Technical Summary of System

As with the IHC process. The trained machine learning model 30 which is produced via mIF informed labeling in the method described in section 3.2.2 can be incorporated into the system 40 for identification and classification of biological structures described in section 3.1.2

3.2.4 Key Aspects of the mIF Workflow that Differ from the IHC mIF stainings typically are done first- and then the base (H&E) stain is done second. There is no stain removal process 4 applied between the two stainings when this order of the stainings is used. This approach is commonly employed because H&E is autofluorescent, which can create problems if performed first.

It is however also possible to use mIF as the informer image 6, and to perform this staining after the H&E staining and image generation. This approach is more complex as additional work-arounds must be built into the process to prevent autofluorescence from the initial H&E stain from negatively impacting the subsequent mIF image generation steps.

The coregistration process can be performed differently due to the different staining modality.

The label extraction process can be different due to the different types of stainings used.

3.2.5 Examples of Improvements Provided by the Described Approach

Consistent with disclosed embodiments, an automated label extraction process can be implemented using the mIF images. Like for the automated label extraction techniques described for IHC: Automated mIF label has the same advantage of reducing work-load and human error as compared with human-expert created annotations. Both rule-based and deep-learning based approaches to automated label extraction from mIF images have already been successfully demonstrated by the applicant.

The quality and accuracy of the generated labels can be ensured by only including those labels/predictions of the automated label extraction process that have a high probability of being correct. One approach to doing this is by only accepting those labels where a confidence value assigned during the automatic label extraction process for each object is higher than a certain threshold value. The automatic label extraction process can for example exhibit this type of confidence value by forwarding the (calibrated) probability/confidence/likelihood values of a machine learning model. The quality of such a cutoff can be determined by comparing it to reference evaluation annotations.

mIF with 12 or more stains offers a vast depth of information about the composition of the sample being studied. Far more than IHC (even multiplex chromogenic immunohistochemistry) can generally offer for a single piece of tissue.

4. An Example of a Pipeline for Implementing the Described Approach

Figure 11:
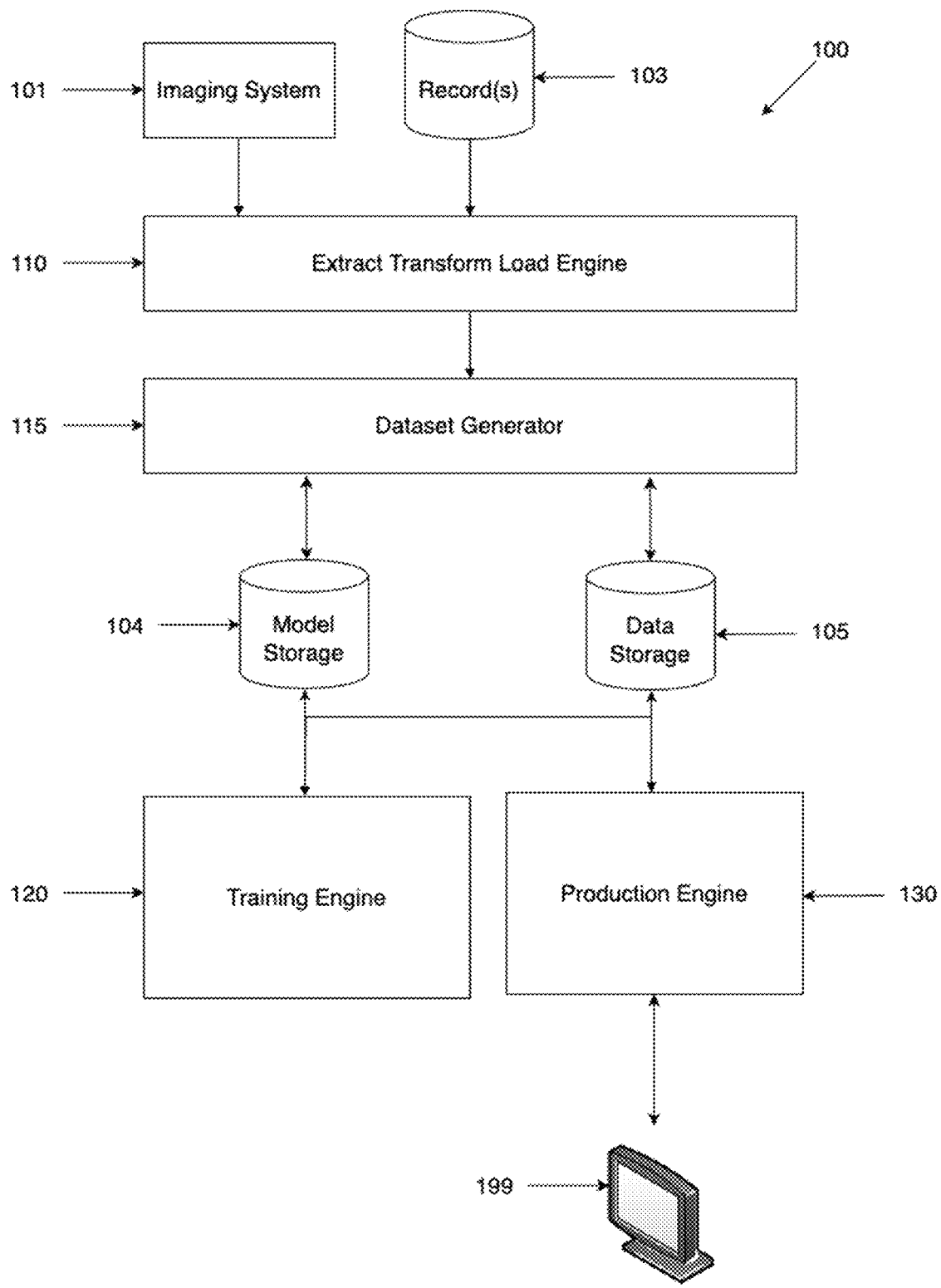
FIG. 11 shows an example of a pipeline for developing, validating, and deploying machine learning models for identifying or classifying biological structures, in accordance with disclosed embodiments.

FIG. 11 depicts an example of a pipeline 100 for developing, validating, and deploying machine learning models for identifying or classifying biological structures, consistent with disclosed embodiments. The pipeline 100 is solely provided as an example, and the particular structure of this pipeline 100, and the configuration of its components, is not intended to be limiting. It is envisaged that this pipeline may take many other forms, for example, any component of this pipeline may be excluded, and any number of additional components may be introduced.

Pipeline 100 can include components from which data is originally obtained, such as imaging system 101 or record(s) 103. Such data can include image data depicting biological structures (e.g., video or picture data or a biological sample, such as a histological sample).

Pipeline 100 can include components, such as extract transform load (ETL) engine 110, for the collection and preparation of the obtained data. For example, ETL engine 110 can be configured to obtain and process image data for inclusion in a training or production dataset, as described herein.

Pipeline 100 can include components, such as data storage 105 and model storage 104, for the storage of datasets and models (e.g., machine-learning models, rule-based models, or the like). Such models can include detection models, labeling models, or classification models as described herein. Pipeline 100 can include training engine 120 for generating trained machine-learning models using obtained datasets and models. Pipeline 100 can include production engine 130 for using trained-machine learning models to identify or classify biological structures depicted in provided image data. Components of pipeline 100 can be managed and configured through a user device 199. User device 199 can also be used to display outputs of other components, original or prepared data, trained or untrained models, or indications of identified or classified biological structures. A user can interact with components of pipeline 100 to perform model validation and development, consistent with disclosed embodiments. In some embodiments, a user can interact with training engine 120 (or another suitable component of pipeline 100) to perform model development. Likewise, in some embodiments, a user can interact with production engine 130 (or another suitable component of pipeline 100) to apply a detection, labeling, or classification model. Overall, pipeline 100 can provide a convenient, scalable, platform for developing, validating, and deploying models for the detection and classification of biological structures in digital pathology.

Imaging system 101 can be a device suitable for obtaining image data depicting a biological sample, for example the imaging system 101 may comprise a microscope suitable for use in pathology, and a digital scanner configured to digitize histopathological slides. Such an imaging system 101 can be configured to acquire video or images of a biological sample. The imaging system 101 can be configured to visualize the biological sample under a range of lighting conditions (e.g., fluorescence, visual light, or the like) and magnifications. As may be appreciated, pipeline 100 is not limited to embodiments in which imaging system 101 comprises a microscope suitable for use in pathology, and a digital scanner configured to digitize histopathological slides. Furthermore, in some embodiments, rather than providing data directly to ETL engine 110, imaging system 101 can provide data to record(s) 103. ETL engine 110 can then obtain this data from record(s) 103.

Consistent with disclosed embodiments, record(s) 103 can include one or more storage locations for data usable by pipeline 100 to identify or classify biological structure(s) in an image of a biological sample. In some embodiments, such data can include video data or images acquired by imaging system 101 from the biological sample. In various embodiments such data can include medical record information from the patients from which the biological samples were obtained. Such medical record information can include medical records, case notes, request, requisition information (e.g., pertaining to the biological sample or to biological structures present or potentially present within the biological sample) or results of analytical tests provided by a physician or other clinician. In some embodiments, the medical record information can include class or data label information corresponding to the biological samples (e.g., for use in generating training datasets).

Consistent with disclosed embodiments, the medical record information can be associated with biological samples. For example, in a cancer screening or diagnosis setting, the medical record information can include data associated with a cancer type, a cancer prevalence, a cancer prognosis, or a cancer stage associated with the biological sample or the patient from which the biological sample was obtained. As an additional example, medical record information concerning a biological sample can include labels for video or image data of the biological sample. Such labels may have been generated by a human expert, a rule based model, a machine learning model, or the like. As described herein, such labels may be a graphical effect overlaid on the video or image data of the biological sample, a graphical indicator or alphanumeric label associated with the video or image data of the biological sample, or one or more coordinates indicating locations of biological structures in the video or image data.

Consistent with disclosed embodiments, ETL engine 110 can be configured to obtain data in varying formats from one or more sources (e.g., imaging system 101, record(s) 103, or the like). The disclosed embodiments are not limited to any particular format of the obtained data, or method for obtaining this data. For example, the obtained data can be or include structured data or unstructured data. ETL engine 110 can interact with the various data sources to receive or retrieve the data. ETL engine 110 can transform the data into suitable format(s) and load the transformed data into a target component or database of pipeline 100.

In some embodiments, transforming the data can include cleaning, structuring, enriching, or converting the data into a format consistent with any requirements of pipeline 100. In some embodiments, ETL engine 110 can perform quality control processing on obtained image data. Such quality control processing can include confirming that image data is usable (e.g., verifying magnification, identifying, and potentially compensating for blurriness or artifacts, discarding image data, or portions of image data likely to interfere with correct label extracting, or the like) or correcting for problems with the image data.

In some embodiments, ETL engine 110 can process the data into standard formats (e.g., into a standard color model or image file format, a standard brightness (e.g., average or range) or contrast, a standard resolution or image size, or the like). Accordingly, ETL engine 110 can clean the obtained data such that the data, although originating from a variety of different sources, has a consistent format.

In some embodiments, ETL engine 110 can generate a standard structure containing an item of image data. For example, pipeline 100 can be configured to maintain a set of data objects (e.g., an array or database of such data objects), each data object containing image data concerning a biological sample and metadata concerning the biological sample (e.g., medical record information corresponding to the item of image data, or the like). As an additional example, pipeline 100 can be configured to maintain a set of images for biological samples, a set of metadata concerning the biological samples, and a concordance between the two sets (e.g., an array of sample images, an array of sample metadata, and an express or implicit mapping of the indices of one array to the indices of the other array).

In some embodiments, ETL engine 110 can enrich image data or medical record information by generating additional data using the image data or medical record information. For example, as described herein, ETL engine 110 can coregister base and informer images, as described herein, to generate paired sets of base and informer image(s). As an additional example, ETL engine 110 can detect biological structures within an image (or paired images) and generate separate images (or separate paired images), each including one or more detected biological structures.

Consistent with disclosed embodiments, ETL engine 110 can load the transformed data into another component of pipeline 100, such as dataset generator 115 (or into a suitable data storage, from which dataset generator 115 can retrieve the data).

In some embodiments, dataset generator 115 can be configured to extract features from data received from ETL engine 110. A feature can be a property or characteristics of a phenomenon. For example, the presence or absence of a fluorescent value in excess of a threshold at a location corresponding to a particular protein can be a feature. As an additional example, the average fluorescence value over an image of a biological sample can be a feature. Features can be determined based on the domain, data type of a category, or many other factors associated with data stored in a data structure. Additionally, a feature can represent information about multiple data records in a data set or information about a single category in a data record. Moreover, multiple features can be produced to represent the same data.

In some embodiments, dataset generator 115 can use a labeling model to generate labels for samples. Dataset generator 115 can obtain the labeling model from model storage 104, or the like. The labeling model can be generated using training engine 120, as described herein (or obtained from another system). The labeling model can generate labels for samples as described herein. In some embodiments, the labeling model can generate the labels using images (or paired sets of base and informer image(s)), extracted features, medical record information, or the like.

In some embodiments, dataset generator 115 can be configured to accept labels provided by a user through user device 199. For example, dataset generator 115 can be configured to provide data (or metadata concerning the data)

received from ETL engine 110 to user device 199 for display. In response, dataset generator 115 can receive label information. For example, dataset generator 115 can provide base and informer image(s) of a biological sample and medical records associated with the biological sample to user device 199. In response, a user can interact with user device 199 to provide annotations of the base or informer image. The annotations can correspond to biological structures in the biological sample.

Consistent with disclosed embodiments, dataset generator 115 can be configured to generate datasets using the transformed data generated by ETL engine 110. In some embodiments, training engine 120 or production engine 130 can be configured to expect datasets having a particular structure. Dataset generator 115 can be configured to format the transformed data into that particular structure. For example, dataset generator 115 can be configured to generate samples including images (or paired sets of base and informer image(s)), label(s), features, or metadata. Dataset generator 115 can be configured to store the samples in data storage 105.

Consistent with disclosed embodiments, model storage 104 can be a storage location for models usable by components of pipeline 100 (e.g., dataset generator 115, training engine 120, or production engine 130). The disclosed embodiments are not limited to any particular implementation of model storage 104. Consistent with disclosed embodiments, model storage 104 can be implemented using one or more relational databases, object-oriented or document-oriented databases, tabular data stores, graph databases, distributed file systems, or other suitable data storage options.

Consistent with disclosed embodiments, data storage 105 can be a storage location for prepared datasets usable by training engine 120 or production engine 130. The disclosed embodiments are not limited to any particular implementation of data storage 105. Consistent with disclosed embodiments, data storage 105 can be implemented using one or more relational databases, object-oriented or document-oriented databases, tabular data stores, graph databases, distributed file systems, or other suitable data storage options.

Consistent with disclosed embodiments, training engine 120 can be configured to train, or create and train, models. Training engine 120 can be configured to create models (e.g., in response to a command to create a trained model of a particular type using an input dataset) or obtain existing models from model storage 104. Training engine 120 can be configured to create or train models using training datasets obtained from data storage 105. In some embodiments, training engine 120 can be configured to store trained models in model storage 104.

Consistent with disclosed embodiments, training engine 120 can include model training and model evaluation components. Training engine 120 can be configured to train a model using a model training component and then determine performance measure values for the model using a model evaluation component.

In some embodiments, training engine 120 can provide a model and a cross-validation or holdout portion of a training dataset to the model evaluation component. In some embodiments, training engine 120 can specify one or more performance measures. Additionally, or alternatively, the model evaluation component can be configured with a predetermined or default set of performance measures. In some embodiments, the performance measures can include confusion matrices, mean-squared-error, mean-absolute-error, sensitivity or selectivity, receiver operating characteristic curves or area under such curves, precision and recall, F-measure, or any other suitable performance measure. In some embodiments, performance measure values can be displayed to a user through user device 199. The user may then interact through user device 199 with training engine 120 to update the model.

In some embodiments, training engine 120 can automatically update the model being trained based on the performance measure values. In various embodiments, training engine 120 can update the model being trained in response to user input provided through user device 199. Updating the model can include one or more of performing additional training (e.g., using the existing training dataset or another training dataset), modifying the model (e.g., changing the input features used by the model, changing the architecture of the model, or the like), or changing the training environment (e.g., changing training hyperparameters, changing a division of the training dataset into training, cross-validation, and holdout portions, or the like).

Consistent with disclosed embodiments, production engine 130 can be configured to identify or classify biological structures in patient data using a trained classification model. In some embodiments, production engine 130 can obtain the trained classification model from model storage 104. In some embodiments, production engine 130 can obtain the patient data from data storage 140. In some embodiments, production engine 130 can obtain the patient data from another data storage location. This alternative data storage location can be associated with another entity or user. For example, production engine 130 can receive or retrieve the patient data from a healthcare system controlled by an entity distinct from the entity that controls production engine 130.

Consistent with disclosed embodiments, the patient data can include a base image. The production engine 130 can apply the base image to the trained classification model to provide as output an indication when a biological structure is identified or classified in the base image. Consistent with disclosed embodiments, the indication can be an annotated version of the base image, an indication of the presence of the biological structure, or the like. The indication can be provided by production engine 130 to user device 199. In some embodiments, the indication can be stored on a computing device associated with pipeline 100 or provided to another system.

Consistent with disclosed embodiments, user device 199 can provide a user interface for interacting with other components of pipeline 100. The user interface can be a graphical user interface. The user interface can enable a user to configure ETL engine 110 to extract, transform, and load data according to user specifications. The user interface can enable the user to specify how the transformed data received by dataset generator 115 is converted into labeled training data (or suitable patient data). In some embodiments, the user interface can enable the user to interact with dataset generator 115 to manually or semi-manually label or annotate the training data. In some embodiments, the user interface can enable a user to provide data or models to training engine 120 for training, or to production engine 130 for identification and classification.

In some embodiments, the user interface can enable a user to interact with training engine 120 to create or select a model for training, create or select a dataset for use in training the model, or select training parameters or hyperparameters. In some embodiments, the user interface can enable a user to interact with training engine 120 to display information related to training of the model (e.g., performance measure values, a change in loss function values during training, or other training information). In some embodiments, the user interface can enable a user to interact with production engine 130 to select a training model and patient data (e.g., a base image). In some embodiments, the user interface can enable a user to interact with production engine 130 to display any indication of an identified biological structure in the patient data, store the indication on a computing device, or transmit the indication to another system.

Components of pipeline 100 can be implemented using one or more computing devices. Such computing devices can include tablets, laptops, desktops, workstations, computing clusters, or cloud computing platforms. In some embodiments, components of pipeline 100 can be implemented using cloud computing platforms. For example, one or more of ETL engine 110, dataset generator 115, training engine 120, and production engine 130 can be implemented on a cloud computing platform. In some embodiments, components of pipeline 100 can be implemented using on-premises systems. For example, imaging system 101, record(s) 103, or user device 199 can be, or be hosted on, on-premises systems. As an additional example, model storage 104 or data storage 105 can be, or be hosted on, on-premises systems.

Components of pipeline 100 can communicate using any suitable method. In some embodiments, two or more components of pipeline 100 can be implemented as microservices or web services. Such components can communicate using messages transmitted on a computer network. The messages can be implemented using SOAP, XML, HTTP, JSON, RCP, or any other suitable format. In some embodiments, two or more components of pipeline 100 can be implemented as software, hardware, or combined software/hardware modules. Such components can communicate using data or instructions written to or read from a memory (e.g., a shared memory), function calls, or any other suitable communication method.

As may be appreciated, the particular structure of pipeline 100 is not intended to be limiting. Consistent with disclosed embodiments, any two or more of record(s) 103, model storage 104, or data storage 105 can be combined, or hosted on the same computing device. Consistent with disclosed embodiments, ETL engine 110 and dataset generator 115 can be omitted from pipeline 100. In such embodiments, datasets formatted and configured for use by training engine 120 or production engine 130 can be deposited in data storage 105 by another system or using another method. Consistent with disclosed embodiments, ETL engine 110 and dataset generator 115 can be combined. In such embodiments, data extraction, transformation, and loading can be combined with feature extraction, labeling, and sample creation. Consistent with disclosed embodiments, training engine 120 and production engine 130 can be combined.

Though shown with one user device 199, pipeline 100 could have multiple user devices. Different user devices could be associated with different entities or different users having different roles. For example, user device 199 could be associated with a software engineer or data scientist who is developing the test, while another user device could be associated with a clinician who is using the test.

User device 199 can be combined with one or more other components of pipeline 100. In some embodiments, user device 199 and at least one of ETL engine 110, dataset generator 115, training engine 120, or production engine 130 can be implemented by the same computing device. In various embodiments, user device 199 and at least one of model storage 104 or data storage 105 can be implemented by the same computing device.

As may be appreciated, pipeline 100 can be integrated into a method for treating patients with a particular health condition. Production engine 130 can use a trained classification model and input data obtained from a patient sample to determine whether the patient is experiencing a negative health outcome. For example, the trained predictive model and input data obtained from a patient sample can be used in the detection of pathological abnormalities indicative of disease, the diagnosis of disease type/subtype, the staging of disease progression or recommendation of suitable therapy options. Examples of these include detection of tumor cells within a tissue sample, assignment of the specific cancer subtype, assignment of cancer stage and/or metastasis risk, best probability therapy recommendations based on the assimilated knowledge of the subtype, progression and case-specific tumor composition and physiological reaction. If the patient has a particular diagnosis, or a risk greater than (or potentially equal to) a health-outcome dependent threshold, then the patient can be treated or monitored according to a first, more-aggressive or intensive protocol. If the patient lacks the diagnosis or has a risk less than (or potentially equal to) the health-outcome dependent threshold, then the patient can be treated or monitored according to a second, less-aggressive or intensive protocol.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Embodiments herein include systems, methods, and tangible non-transitory computer-readable media. The methods may be executed, at least in part for example, by at least one processor that receives instructions from a tangible non-transitory computer-readable storage medium. Similarly, systems consistent with the present disclosure may include at least one processor and memory, and the memory may be a tangible non-transitory computer-readable storage medium. As used herein, a tangible non-transitory computer-readable storage medium refers to any type of physical memory on which information or data readable by at least one processor may be stored. Examples include random access memory (RAM), read-only memory (ROM), volatile memory, non-volatile memory, hard drives, CD ROMs, DVDs, flash drives, disks, registers, caches, and any other known physical storage medium. Singular terms, such as "memory" and "computer-readable storage medium," may additionally refer to multiple structures, such a plurality of memories or computer-readable storage media. As referred to herein, a "memory" may comprise any type of computer-readable storage medium unless otherwise specified. A computer-readable storage medium may store instructions for execution by at least one processor, including instructions for causing the processor to perform steps or stages consistent with embodiments herein. Additionally, one or more computer-readable storage media may be utilized in implementing a computer-implemented method. The term "non-transitory computer-readable storage medium" should be understood to include tangible items and exclude carrier waves and transient signals.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure. Therefore, it is intended that the disclosed embodiments and examples be considered as examples only, with a true scope of the present disclosure being indicated by the following claims and their equivalents.

The embodiments may further be described using the following clauses:

1. A method for generating a machine learning model for identifying or classifying biological structures depicted in a base image, comprising: obtaining a first training dataset, the first training dataset including first sets of coregistered images of biological structures, each first set including a first base image and a first informer image, and being associated with first label data; training, using the first training dataset, a label generation model, the label generation model configured to accept as input a second set of coregistered images and to produce as output second label data corresponding to the second set of coregistered images, the second set of coregistered images including a second base image and a second informer image; generating a second training dataset using the label generation model, the second training dataset including the second base images and the second label data; and training, using the second training dataset, a classification model configured to accept as input a third base image and to provide as output an indication when a biological structure is identified or classified in the third base image.

2. The method of clause 1, wherein: the first training dataset is obtained by: obtaining a preliminary dataset including fourth sets of images of the biological structures, each fourth set including a fourth base image and a fourth informer image; applying, for each fourth set, the fourth base image to an object detection model trained to detect the biological structures to generate the corresponding first base image, the first base image being a cropped version of the fourth base image; and generating the first sets of the coregistered images of the biological structures using the fourth informer images and the first base images.

3. The method of clause 2, wherein: the first training dataset is further obtained by filtering the first base images based on: misalignment with corresponding cropped versions of the fourth informer images; depiction of necrotic tissue or anthracosis deposits; or a distance between a depicted biological structure in a first base image and a biological tissue border; or the second training dataset is further generated by filtering the second base images based on: depiction of necrotic tissue or anthracosis deposits; or a distance between a depicted biological structure in a second base image and a biological tissue border.

4. The method of any one of clauses 2 to 3, wherein: the first training dataset is further obtained by filtering the first base images using exclusion rules; or the second training dataset is further generated by filtering the second base images using the exclusion rules.

5. The method of any one of clauses 1 to 4, wherein: the first training dataset is obtained by: applying detection rules to a preliminary dataset including fourth sets of images of the biological structures, each fourth set including a fourth base image and a fourth informer image, to generate the corresponding first base image, the first base image being a cropped version of the fourth base image.

6. The method of any one of clauses 1 to 5, wherein: the first training dataset is obtained by: generating the first label data by applying labeling rules to the first sets of coregistered images of the biological structures.

7. The method of clause 6, wherein: the labeling rules depend upon at least one of cell nucleus size, hematoxylin stain intensity of cell nucleus in H&E stain, sphericity or circularity of the nucleus, estimation of the cytoplasm region and cytoplasm stain intensity, eosin staining intensity of cytoplasm in H&E stain, ratio of estimated cytoplasm size to the cell nucleus size.

8. The method of any one of clauses 1 to 7, wherein: the second base image comprises an image of biological material stained with hematoxylin and eosin; the second informer image comprises an image of the biological material stained with at least one of an immunohistochemistry stain, an immunofluorescence stain, or a multi-chromogenic immunofluorescence stain; and the biological material is stained with the at least one of the immunohistochemistry stain, the immunofluorescence stain, or the multi-chromogenic immunofluorescence stain after application of a removal agent to the biological material to remove the hematoxylin and eosin stain.

9. The method of any one of clauses 1 to 7, wherein: the second base image comprises an image of biological material stained with hematoxylin and eosin; the second informer image comprises an image of the biological material stained with an immunofluorescence stain; and the second base image is captured after the second informer image is captured.

10. The method of any one of clauses 1 to 9, wherein: the label generation model or the classification model comprises a convolutional neural network, residual neural network, or transformer neural network.

11. The method of any one of clauses 1 to 10, wherein: the biological structures comprise nuclei, tubuli, nerves, arteries or any other blood vessels, single cells, cells or glomeruli.

12. The method of any one of clauses 1 to 11, wherein: the first label data, the second label data, or the indication comprises at least one of: a graphical effect overlaid on the first base image, the second base image, or the third base image, respectively; a graphical indicator or alphanumeric label associated with the first base image, the second base image, or the third base image, respectively; or one or more coordinates indicating locations of biological structures in the first base image, the second base image, or the third base image, respectively.

13. A system comprising: at least one processor; and at least one computer-readable medium containing instructions that, when executed by the at least one processor, cause the system to perform operations comprising: obtaining a first image stained using a first stain; generating an indication of a biological structure identified or classified in the first image by applying the first image to a classification model, the classification model trained to accept as input a second image stained using the first stain and produce as output an indication when a biological structure is identified or classified in the input second image, the classification model trained using a label generation model configured to accept as input a set of third images and produce as output label data, the set of third images including a third image stained with the first stain and a third image stained with a second stain; and providing the indication.

14. The system of clause 13, wherein: the first image is obtained by: obtaining a fourth image; applying the fourth image to an object detection model trained to detect the biological structures to generate corresponding one or more candidate first images, the one or more candidate first images being cropped versions of the fourth image.

15. The system of clause 14, wherein: the first image is obtained by filtering the one or more candidate first images based on: depiction of necrotic tissue or anthracosis deposits; or a distance between a depicted biological structure in a candidate first image and a biological tissue border.

16. The system of any one of clauses 14 to 15, wherein: the first image is obtained by filtering the one or more candidate first images using exclusion rules.

17. The system of any one of clauses 13 to 16, wherein: the third image stained with the first stain comprises an image of biological material stained with hematoxylin and eosin; the third image stained with the second stain comprises an image of the biological material stained with at least one of an immunohistochemistry stain, an immunofluorescence stain, or a multi-chromogenic immunofluorescence stain; and the biological material is stained with the at least one of the immunohistochemistry stain, the immunofluorescence stain, or the multi-chromogenic immunofluorescence stain after application of a removal agent to the biological material to remove the hematoxylin and eosin stain.

18. The system of any one of clauses 13 to 16, wherein: the third image stained with the first stain comprises an image of biological material stained with hematoxylin and eosin; the third image stained with the second stain comprises an image of the biological material stained with an immunofluorescence stain; and the third image stained with the first stain is captured after the third image stained with the second stain is captured.

19. The system of any one of clauses 13 to 18, wherein: the label generation model or the classification model comprises a convolutional neural network, residual neural network, or transformer neural network.

20. The system of any one of clauses 13 to 19, wherein: the biological structures comprise nuclei, tubuli, nerves, arteries or any other blood vessels, single cells, cells or glomeruli.

21. The system of any one of clauses 13 to 20, wherein: the indication comprises at least one of: a graphical effect overlaid on the first image; a graphical indicator or alphanumeric label associated with the first image; or one or more coordinates indicating locations of biological structures in the first image.

22. The system of any one of clauses 13 to 21, wherein: the indication is provided to a display or user interface, a storage location, or a second system.

23. A computer-readable medium containing instructions that, when executed by at least one processor of a system, cause the system to perform operations comprising: obtaining a first image stained using a first stain; generating an indication of a biological structure identified or classified in the first image by applying the first image to a classification model, the classification model trained to accept as input a second image stained using the first stain and produce as output an indication when a biological structure is identified or classified in the input second image, the classification model trained using a label generation model configured to accept as input a set of third images and produce as output label data, the set of third images including a third image stained with the first stain and a third image stained with a second stain; and providing the indication.

24. The computer-readable medium of clause 23, wherein: the first image is obtained by: obtaining a fourth image; applying the fourth image to an object detection model trained to detect the biological structures to generate corresponding one or more candidate first images, the one or more candidate first images being cropped versions of the fourth image.

25. The computer-readable medium of clause 24, wherein: the first image is obtained by filtering the one or more candidate first images based on: depiction of necrotic tissue or anthracosis deposits; or a distance between a depicted biological structure in a candidate first image and a biological tissue border.

26. The computer-readable medium of any one of clauses 24 to 25, wherein: the first image is obtained by filtering the one or more candidate first images using exclusion rules.

27. The computer-readable medium of any one of clauses 23 to 26, wherein: the third image stained with the first stain comprises an image of biological material stained with hematoxylin and eosin; the third image stained with the second stain comprises an image of the biological material stained with at least one of an immunohistochemistry stain, an immunofluorescence stain, or a multi-chromogenic immunofluorescence stain; and the biological material is stained with the at least one of the immunohistochemistry stain, the immunofluorescence stain, or the multi-chromogenic immunofluorescence stain after application of a removal agent to the biological material to remove the hematoxylin and eosin stain.

28. The computer-readable medium of any one of clauses 23 to 26, wherein: the third image stained with the first stain comprises an image of biological material stained with hematoxylin and eosin; the third image stained with the second stain comprises an image of the biological material stained with an immunofluorescence stain; and the third image stained with the first stain is captured after the third image stained with the second stain is captured.

29. The computer-readable medium of any one of clauses 23 to 28, wherein: the label generation model or the classification model comprises a convolutional neural network, residual neural network, or transformer neural network.

30. The computer-readable medium of any one of clauses 23 to 29, wherein: the biological structures comprise nuclei, tubuli, nerves, arteries or any other blood vessels, single cells, cells or glomeruli.

31. The computer-readable medium of any one of clauses 23 to 30, wherein: the indication comprises at least one of: a graphical effect overlaid on the first image; a graphical indicator or alphanumeric label associated with the first image; or one or more coordinates indicating locations of biological structures in the first image.

32. The computer-readable medium of any one of clauses 23 to 31, wherein: the indication is provided to a display or user interface, a storage location, or a second system.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

Other embodiments will be apparent from consideration of the specification and practice of the embodiments disclosed herein. It is intended that the specification and examples be considered as example only, with a true scope and spirit of the disclosed embodiments being indicated by the following claims.

Appendix A

The following list contains a structured high-level description of certain disclosed embodiments. The description is presented in the form of a group of structures and interrelated embodiments.

| Comment | Embodiment |
|---|---|
| "Most" general | A method for labeling a base image with knowledge from an informer image. |
| Narrowed to labeling biological structures | A method for labeling biological structures in a base image with knowledge from an informer image. |
| Outline basic embodiment | A method for labeling biological structures in a base image with knowledge from an informer image where:<br>A. a processor A identifies a number of biological structures in the base image<br>B. the base image is coregistered with the informer image<br>C. a processor B labels each biological structure by considering the structure's location in the informer image or in the base and the informer image |
| Extend with quality check | Any embodiment above where the processor B labeling the biological structures only considers structures which lie in a location which is deemed suitable for labeling the structure |
| Extend with number of quality checks | Any embodiment above where the consideration of if a location is deemed suitable is based on a number of suitability checks which need to be fulfilled. |
| Extend with quality check method | Any embodiment above where a suitability check of if a location is deemed suitable is based on:<br>A. a human expert<br>B. an algorithm<br>C. an algorithm that considers the neighborhood of the location in the base and the informer image<br>D. the inclusion of the location in a given region of interest<br>E. a machine learning model |
| Specify quality checks | Any embodiment above where any of the suitability checks if:<br>A. the location is sufficiently well registered to label the according structure<br>B. the tissue is intact at the location in the second image<br>C. the informer stain quality is sufficient at the given location<br>D. the location in the informer stain not in or not too close to a necrotic region. |
| Extend with specifying processor A | Any embodiment above where the processor A is:<br>A. a human expert<br>B. an algorithm<br>C. an algorithm based on computer vision image features<br>D. a machine learning model |
| Extend with specifying processor B | Any embodiment above where the processor B is:<br>E. a human expert<br>F. an algorithm<br>G. an algorithm based on computer vision image features<br>H. a machine learning model |
| Extend with specifying processor B with trained model | Any embodiment above where the processor B is a machine learning model and is trained with labels gathered where a human expert labeled a number of biological structures by considering the informer image or the base and the informer image. |
| Extend with application of gathered labels | Any embodiment above where the labels generated by processor B for the biological structures in the base image are used to train a machine learning model C to predict the label of the structure from locations in the base image. |
| Extend to standalone inference | Any embodiment above where the processor A and the machine learning model C are combined into a processor for labeling base images. |

What is claimed is:

1. A system comprising:
   at least one processor; and
   at least one computer-readable medium containing instructions that, when executed by the at least one processor, cause the system to perform operations comprising:
   obtaining a first image stained using a first stain;
   generating an indication of a biological structure identified or classified in the first image by applying the first image to a classification model, the classification model trained to accept as input a second image stained using the first stain and produce as output the indication when the biological structure is identified or classified in the input second image, the classification model trained using a label generation model configured to accept as input a set of third images and produce as output label data, the set of the third images including a third image stained with the first stain and a third image stained with a second stain; and
   providing the indication.

2. The system of claim 1, wherein:
   the first image is obtained by:
   obtaining a fourth image; and
   applying the fourth image to an object detection model trained to detect the biological structure to generate corresponding one or more candidate first images, the one or more candidate first images being cropped versions of the fourth image.

3. The system of claim 2, wherein:
   the first image is obtained by filtering the one or more candidate first images based on:
   depiction of necrotic tissue or anthracosis deposits; or
   a distance between a depicted biological structure and a biological tissue border.

4. The system of claim 2, wherein:
   the first image is obtained by filtering the one or more candidate first images using exclusion rules.

5. The system of claim 1, wherein:
   the third image stained with the first stain comprises an image of biological material stained with hematoxylin and eosin;
   the third image stained with the second stain comprises an image of the biological material stained with at least one of an immunohistochemistry stain, an immunofluorescence stain, or a multi-chromogenic immunofluorescence stain; and
   the biological material is stained with the at least one of the immunohistochemistry stain, the immunofluorescence stain, or the multi-chromogenic immunofluorescence stain after application of a removal agent to the biological material to remove the hematoxylin and eosin stain.

6. The system of claim 1, wherein:
   the third image stained with the first stain comprises an image of biological material stained with hematoxylin and eosin;
   the third image stained with the second stain comprises an image of the biological material stained with an immunofluorescence stain; and
   the third image stained with the first stain is captured after the third image stained with the second stain is captured.

7. The system of claim 1, wherein:
   the label generation model or the classification model comprises a convolutional neural network, residual neural network, or transformer neural network.

8. The system of claim 1, wherein:
   the biological structure comprises a nucleus, tubule, nerve, artery or other blood vessel, single cell, group of cells, or glomerulus.

9. The system of claim 1, wherein:
   the indication comprises at least one of:
   a graphical effect overlaid on the first image;
   a graphical indicator or alphanumeric label associated with the first image; or
   one or more coordinates indicating a location of the biological structure in the first image.

10. The system of claim 1, wherein:
    the indication is provided to a display or user interface, a storage location, or a second system.

11. A method, comprising:
    obtaining a first image stained using a first stain;
    generating an indication of a biological structure identified or classified in the first image by applying the first image to a classification model, the classification model trained to accept as input a second image stained using the first stain and produce as output the indication when the biological structure is identified or classified in the input second image, the classification model trained using a label generation model configured to accept as input a set of third images and produce as output label data, the set of the third images including a third image stained with the first stain and a third image stained with a second stain; and providing the indication.

12. The method of claim 11, wherein:
    the first image is obtained by:
    obtaining a fourth image; and
    applying the fourth image to an object detection model trained to detect the biological structure to generate corresponding one or more candidate first images, the one or more candidate first images being cropped versions of the fourth image.

13. The method of claim 12, wherein:
    the first image is obtained by filtering the one or more candidate first images based on:
    depiction of necrotic tissue or anthracosis deposits; or
    a distance between a depicted biological structure and a biological tissue border.

14. The method of claim 12, wherein:
    the first image is obtained by filtering the one or more candidate first images using exclusion rules.

15. The method of claim 11, wherein:
    the third image stained with the first stain comprises an image of biological material stained with hematoxylin and eosin;
    the third image stained with the second stain comprises an image of the biological material stained with at least one of an immunohistochemistry stain, an immunofluorescence stain, or a multi-chromogenic immunofluorescence stain; and
    the biological material is stained with the at least one of the immunohistochemistry stain, the immunofluorescence stain, or the multi-chromogenic immunofluorescence stain after application of a removal agent to the biological material to remove the hematoxylin and eosin stain.

16. The method of claim 11, wherein:
the third image stained with the first stain comprises an image of biological material stained with hematoxylin and eosin;
the third image stained with the second stain comprises an image of the biological material stained with an immunofluorescence stain; and
the third image stained with the first stain is captured after the third image stained with the second stain is captured.

17. The method of claim 11, wherein:
the label generation model or the classification model comprises a convolutional neural network, residual neural network, or transformer neural network.

18. The method of claim 11, wherein:
the biological structure comprises a nucleus, tubule, nerve, artery or other blood vessel, single cell, group of cells, or glomerulus.

19. The method of claim 11, wherein:
the indication comprises at least one of:
  a graphical effect overlaid on the first image;
  a graphical indicator or alphanumeric label associated with the first image; or
  one or more coordinates indicating a location of the biological structure in the first image.

20. The method of claim 11, wherein:
the indication is provided to a display or user interface, a storage location, or a second system.

21. A non-transitory, computer-readable medium containing instructions that, when executed by at least one processor of a system, cause the system to perform operations comprising:
obtaining a first image stained using a first stain;
generating an indication of a biological structure identified or classified in the first image by applying the first image to a classification model, the classification model trained to accept as input a second image stained using the first stain and produce as output the indication when the biological structure is identified or classified in the input second image, the classification model trained using a label generation model configured to accept as input a set of third images and produce as output label data, the set of the third images including a third image stained with the first stain and a third image stained with a second stain; and
providing the indication.

22. The non-transitory, computer-readable medium of claim 21, wherein:
the first image is obtained by:
  obtaining a fourth image; and
  applying the fourth image to an object detection model trained to detect the biological structure to generate corresponding one or more candidate first images, the one or more candidate first images being cropped versions of the fourth image.

23. The non-transitory, computer-readable medium of claim 22, wherein:
the first image is obtained by filtering the one or more candidate first images based on:
  depiction of necrotic tissue or anthracosis deposits; or
  a distance between a depicted biological structure and a biological tissue border.

24. The non-transitory, computer-readable medium of claim 22, wherein:
the first image is obtained by filtering the one or more candidate first images using exclusion rules.

25. The non-transitory, computer-readable medium of claim 21, wherein:
the third image stained with the first stain comprises an image of biological material stained with hematoxylin and eosin;
the third image stained with the second stain comprises an image of the biological material stained with at least one of an immunohistochemistry stain, an immunofluorescence stain, or a multi-chromogenic immunofluorescence stain; and
the biological material is stained with the at least one of the immunohistochemistry stain, the immunofluorescence stain, or the multi-chromogenic immunofluorescence stain after application of a removal agent to the biological material to remove the hematoxylin and eosin stain.

26. The non-transitory, computer-readable medium of claim 21, wherein:
the third image stained with the first stain comprises an image of biological material stained with hematoxylin and eosin;
the third image stained with the second stain comprises an image of the biological material stained with an immunofluorescence stain; and
the third image stained with the first stain is captured after the third image stained with the second stain is captured.

27. The non-transitory, computer-readable medium of claim 21, wherein:
the label generation model or the classification model comprises a convolutional neural network, residual neural network, or transformer neural network.

28. The non-transitory, computer-readable medium of claim 21, wherein:
the biological structure comprises a nucleus, tubule, nerve, artery or other blood vessel, single cell, group of cells, or glomerulus.

29. The non-transitory, computer-readable medium of claim 21, wherein:
the indication comprises at least one of:
  a graphical effect overlaid on the first image;
  a graphical indicator or alphanumeric label associated with the first image; or
  one or more coordinates indicating a location of the biological structure in the first image.

30. The non-transitory, computer-readable medium of claim 21, wherein:
the indication is provided to a display or user interface, a storage location, or a second system.

* * * * *